US007842377B2

(12) United States Patent
Lanphere et al.

(10) Patent No.: US 7,842,377 B2
(45) Date of Patent: *Nov. 30, 2010

(54) POROUS POLYMERIC PARTICLE COMPRISING POLYVINYL ALCOHOL AND HAVING INTERIOR TO SURFACE POROSITY-GRADIENT

(75) Inventors: Janel Lanphere, Newton, MA (US); Ernest J. St. Pierre, South Attleboro, MA (US); Greg Kapoglis, Salem, MA (US); Thomas V. Casey, II, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 119 days.

This patent is subject to a terminal disclaimer.

(21) Appl. No.: 12/236,051

(22) Filed: Sep. 23, 2008

(65) Prior Publication Data

US 2009/0030117 A1   Jan. 29, 2009

Related U.S. Application Data

(63) Continuation of application No. 10/637,130, filed on Aug. 8, 2003, now Pat. No. 7,449,236.

(51) Int. Cl.
*B32B 5/16* (2006.01)
*A61K 31/745* (2006.01)
*A61K 31/80* (2006.01)
*A61K 9/14* (2006.01)

(52) U.S. Cl. .................. 428/212; 424/489; 424/493; 424/501; 428/304.4; 428/310.5; 514/951; 514/964

(58) Field of Classification Search ................ 428/402, 428/212, 304.4, 310.5; 424/489, 493, 501; 514/951, 964
See application file for complete search history.

(56) References Cited

U.S. PATENT DOCUMENTS

| 2,275,154 A | 3/1942 | Merrill et al. |
| 2,609,347 A | 9/1952 | Wilson |
| 3,663,470 A | 5/1972 | Nishimura et al. |

(Continued)

FOREIGN PATENT DOCUMENTS

AU    A-76186/98    10/1998

(Continued)

OTHER PUBLICATIONS

"Injectable Tissue Implant Could Repair Ravages of Surgery", Clemson University, Biotech Week, Oct. 22, 2003, p. 117.

(Continued)

*Primary Examiner*—H. (Holly) T Le
(74) *Attorney, Agent, or Firm*—Fish & Richardson P.C.

(57) ABSTRACT

A composition includes a plurality of particles. At least some of the plurality of particles include cross-linked polyvinyl alcohol and have a diameter of about 500 microns or less. The particles have a first average pore size in an interior region, and a second average pore size at a surface region. The first average pore size being greater than the second average pore size. The composition also includes a carrier fluid. The plurality of particles being in the carrier fluid.

23 Claims, 15 Drawing Sheets

U.S. PATENT DOCUMENTS

| | | |
|---|---|---|
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Moiser |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,514,379 A | 5/1996 | Weissleder et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |

| | | | | | |
|---|---|---|---|---|---|
| 5,553,741 A | 9/1996 | Sancoff et al. | 5,899,877 A | 5/1999 | Leibitzki et al. |
| 5,556,391 A | 9/1996 | Cercone et al. | 5,902,832 A | 5/1999 | Van Bladel et al. |
| 5,556,610 A | 9/1996 | Yan et al. | 5,902,834 A | 5/1999 | Porrvik |
| 5,558,255 A | 9/1996 | Sancoff et al. | 5,922,025 A | 7/1999 | Hubbard |
| 5,558,822 A | 9/1996 | Gitman et al. | 5,922,304 A | 7/1999 | Unger |
| 5,558,856 A | 9/1996 | Klaveness et al. | 5,928,626 A | 7/1999 | Klaveness et al. |
| 5,559,266 A | 9/1996 | Klaveness et al. | 5,935,553 A | 8/1999 | Unger et al. |
| 5,567,415 A | 10/1996 | Porter | 5,951,160 A | 9/1999 | Ronk |
| 5,569,193 A | 10/1996 | Hofstetter et al. | 5,957,848 A | 9/1999 | Sutton et al. |
| 5,569,449 A | 10/1996 | Klaveness et al. | 5,959,073 A | 9/1999 | Schlameus et al. |
| 5,569,468 A | 10/1996 | Modi | 6,003,566 A | 12/1999 | Thibault et al. |
| 5,571,182 A | 11/1996 | Ersek et al. | 6,015,546 A | 1/2000 | Sutton et al. |
| 5,580,575 A | 12/1996 | Unger et al. | 6,027,472 A | 2/2000 | Kriesel et al. |
| 5,583,162 A | 12/1996 | Li et al. | 6,028,066 A | 2/2000 | Unger |
| 5,585,112 A | 12/1996 | Unger et al. | 6,047,861 A | 4/2000 | Vidal et al. |
| 5,595,821 A | 1/1997 | Hager et al. | 6,048,908 A | 4/2000 | Kitagawa |
| 5,622,657 A | 4/1997 | Takada et al. | 6,051,247 A | 4/2000 | Hench et al. |
| 5,624,685 A | 4/1997 | Takahashi et al. | 6,056,721 A | 5/2000 | Shulze |
| 5,635,215 A | 6/1997 | Boschetti et al. | 6,056,844 A | 5/2000 | Guiles et al. |
| 5,637,087 A | 6/1997 | O'Neil et al. | 6,059,766 A | 5/2000 | Greff |
| 5,639,710 A | 6/1997 | Lo et al. | 6,063,068 A | 5/2000 | Fowles et al. |
| 5,648,095 A | 7/1997 | Illum et al. | 6,071,495 A | 6/2000 | Unger et al. |
| 5,648,100 A | 7/1997 | Boschetti et al. | 6,071,497 A | 6/2000 | Steiner et al. |
| 5,650,116 A | 7/1997 | Thompson | 6,073,759 A | 6/2000 | Lamborne et al. |
| 5,651,990 A | 7/1997 | Takada et al. | 6,090,925 A | 7/2000 | Woiszwillo et al. |
| 5,653,922 A | 8/1997 | Li et al. | 6,096,344 A | 8/2000 | Liu et al. |
| 5,657,756 A | 8/1997 | Vrba | 6,099,864 A | 8/2000 | Morrison et al. |
| 5,681,576 A | 10/1997 | Henry | 6,100,306 A | 8/2000 | Li et al. |
| 5,695,480 A | 12/1997 | Evans et al. | 6,139,963 A | 10/2000 | Fujii et al. |
| 5,695,740 A | 12/1997 | Porter | 6,149,623 A | 11/2000 | Reynolds |
| 5,698,271 A | 12/1997 | Liberti et al. | 6,160,084 A | 12/2000 | Langer et al. |
| 5,701,899 A | 12/1997 | Porter | 6,162,377 A | 12/2000 | Ghosh et al. |
| 5,715,824 A | 2/1998 | Unger et al. | 6,165,193 A | 12/2000 | Greene, Jr. et al. |
| 5,716,981 A | 2/1998 | Hunter et al. | 6,179,817 B1 | 1/2001 | Zhong |
| 5,718,884 A | 2/1998 | Klaveness et al. | 6,191,193 B1 | 2/2001 | Lee et al. |
| 5,723,269 A | 3/1998 | Akagi et al. | 6,214,331 B1 | 4/2001 | Vanderhoff et al. |
| 5,725,534 A | 3/1998 | Rasmussen | 6,214,384 B1 | 4/2001 | Pallado et al. |
| 5,733,925 A | 3/1998 | Kunz et al. | 6,224,630 B1 | 5/2001 | Bao et al. |
| 5,741,331 A | 4/1998 | Pinchuk | 6,224,794 B1 | 5/2001 | Amsden et al. |
| 5,746,734 A | 5/1998 | Dormandy, Jr. et al. | 6,235,224 B1 | 5/2001 | Mathiowitz et al. |
| 5,752,974 A | 5/1998 | Rhee et al. | 6,238,403 B1 | 5/2001 | Greene, Jr. et al. |
| 5,756,127 A | 5/1998 | Grisoni et al. | 6,245,090 B1 | 6/2001 | Gilson et al. |
| 5,760,097 A | 6/1998 | Li et al. | 6,251,661 B1 | 6/2001 | Urabe et al. |
| 5,766,147 A | 6/1998 | Sancoff et al. | 6,258,338 B1 | 7/2001 | Gray |
| 5,770,222 A | 6/1998 | Unger et al. | 6,261,585 B1 | 7/2001 | Sefton et al. |
| 5,779,668 A | 7/1998 | Grabenkort | 6,264,861 B1 | 7/2001 | Tavernier et al. |
| 5,785,642 A | 7/1998 | Wallace et al. | 6,267,154 B1 | 7/2001 | Felicelli et al. |
| 5,785,682 A | 7/1998 | Grabenkort | 6,268,053 B1 | 7/2001 | Woiszwillo et al. |
| 5,792,478 A | 8/1998 | Lawin et al. | 6,277,392 B1 | 8/2001 | Klein |
| 5,795,562 A | 8/1998 | Klaveness et al. | 6,280,457 B1 | 8/2001 | Wallace et al. |
| 5,797,953 A | 8/1998 | Tekulve | 6,291,605 B1 | 9/2001 | Freeman et al. |
| 5,807,323 A | 9/1998 | Kriesel et al. | 6,296,604 B1 | 10/2001 | Garibaldi et al. |
| 5,813,411 A | 9/1998 | Van Bladel et al. | 6,296,622 B1 | 10/2001 | Kurz et al. |
| 5,823,198 A | 10/1998 | Jones et al. | 6,296,632 B1 | 10/2001 | Luscher et al. |
| 5,827,502 A | 10/1998 | Klaveness et al. | 6,306,418 B1 | 10/2001 | Bley |
| 5,827,531 A | 10/1998 | Morrison et al. | 6,306,419 B1 | 10/2001 | Vachon et al. |
| 5,830,178 A | 11/1998 | Jones et al. | 6,306,425 B1 | 10/2001 | Tice et al. |
| 5,833,361 A | 11/1998 | Funk | 6,306,427 B1 | 10/2001 | Annonier et al. |
| 5,840,387 A | 11/1998 | Berlowitz-Tarrant et al. | 6,312,407 B1 | 11/2001 | Zadno-Azizi et al. |
| 5,846,518 A | 12/1998 | Yan et al. | 6,312,942 B1 | 11/2001 | Plüss-Wenzinger et al. |
| 5,853,752 A | 12/1998 | Unger et al. | 6,315,709 B1 | 11/2001 | Garibaldi et al. |
| 5,855,615 A | 1/1999 | Bley et al. | 6,335,384 B1 | 1/2002 | Evans et al. |
| 5,863,957 A | 1/1999 | Li et al. | 6,344,182 B1 | 2/2002 | Sutton et al. |
| 5,876,372 A | 3/1999 | Grabenkort et al. | 6,355,275 B1 | 3/2002 | Klein |
| 5,877,224 A | 3/1999 | Brocchini et al. | 6,368,658 B1 | 4/2002 | Schwarz et al. |
| 5,885,216 A | 3/1999 | Evans, III et al. | 6,379,373 B1 | 4/2002 | Sawhney et al. |
| 5,885,547 A | 3/1999 | Gray | 6,388,043 B1 | 5/2002 | Langer et al. |
| 5,888,546 A | 3/1999 | Ji et al. | 6,394,965 B1 | 5/2002 | Klein |
| 5,888,930 A | 3/1999 | Smith et al. | 6,423,332 B1 | 7/2002 | Huxel et al. |
| 5,891,155 A | 4/1999 | Irie | 6,432,437 B1 | 8/2002 | Hubbard |
| 5,894,022 A | 4/1999 | Ji et al. | 6,436,112 B2 | 8/2002 | Wensel et al. |
| 5,895,398 A | 4/1999 | Wensel et al. | 6,443,941 B1 | 9/2002 | Slepian et al. |
| 5,895,411 A | 4/1999 | Irie | 6,458,296 B1 | 10/2002 | Heinzen et al. |

| | | | | | |
|---|---|---|---|---|---|
| 6,476,069 B2 | 11/2002 | Krall et al. | EP | 0 730 847 | 9/1996 |
| 6,495,155 B1 | 12/2002 | Tice et al. | EP | 0 744 940 | 12/1996 |
| 6,544,503 B1 | 4/2003 | Vanderhoff et al. | EP | 0 764 047 | 3/1997 |
| 6,544,544 B2 | 4/2003 | Hunter et al. | EP | 0 797 988 | 10/1997 |
| 6,545,097 B2 | 4/2003 | Pinchuk et al. | EP | 0 993 337 | 4/2000 |
| 6,575,896 B2 | 6/2003 | Silverman et al. | ES | 2 096 521 | 3/1997 |
| 6,602,261 B2 | 8/2003 | Greene, Jr. et al. | JP | 59-196738 | 11/1984 |
| 6,602,524 B2 | 8/2003 | Batich et al. | JP | 62-45637 | 2/1987 |
| 6,605,111 B2 | 8/2003 | Bose et al. | JP | 04-057836 | 2/1992 |
| 6,629,947 B1 | 10/2003 | Sahatjian et al. | JP | 4-74117 | 3/1992 |
| 6,632,531 B2 | 10/2003 | Blankenship | JP | 05-076598 | 3/1993 |
| 6,652,883 B2 | 11/2003 | Goupil et al. | JP | 6-57012 | 3/1994 |
| 6,680,046 B1 | 1/2004 | Boschetti | JP | 09-078494 | 3/1997 |
| 6,699,222 B1 | 3/2004 | Jones et al. | JP | 9-110678 | 4/1997 |
| 6,911,219 B2 | 6/2005 | Matson et al. | JP | 9-165328 | 6/1997 |
| 7,053,134 B2 | 5/2006 | Baldwin et al. | JP | 9-316271 | 12/1997 |
| 7,131,997 B2 | 11/2006 | Bourne et al. | JP | 10-130329 | 5/1998 |
| 7,449,236 B2 * | 11/2008 | Lanphere et al. ............ 428/402 | JP | 11-092568 | 4/1999 |
| 7,462,366 B2 * | 12/2008 | Lanphere et al. ............ 424/489 | JP | 2000189511 | 7/2000 |
| 7,501,179 B2 | 3/2009 | Song et al. | JP | 2001079011 | 3/2001 |
| 7,588,780 B2 * | 9/2009 | Buiser et al. ................ 424/501 | JP | 2002-017848 | 1/2002 |
| 7,591,993 B2 | 9/2009 | Boschetti | JP | 2005-521520 | 7/2005 |
| 2001/0001835 A1 | 5/2001 | Greene, Jr. et al. | NZ | 255409 | 2/1997 |
| 2001/0016210 A1 | 8/2001 | Mathiowitz et al. | NZ | 517377 | 8/2003 |
| 2001/0036451 A1 | 11/2001 | Goupil et al. | TW | 421658 | 2/2001 |
| 2001/0051670 A1 | 12/2001 | Goupil et al. | WO | WO 91/12823 | 5/1991 |
| 2002/0054912 A1 | 5/2002 | Kim et al. | WO | WO 92/21327 | 12/1992 |
| 2002/0061954 A1 | 5/2002 | Davis et al. | WO | WO 93/00063 | 1/1993 |
| 2002/0160109 A1 | 10/2002 | Yeo et al. | WO | WO 93/19702 | 10/1993 |
| 2002/0182190 A1 | 12/2002 | Naimark et al. | WO | WO 94/10936 | 5/1994 |
| 2002/0197208 A1 | 12/2002 | Ruys et al. | WO | WO 95/03036 | 2/1995 |
| 2003/0007928 A1 | 1/2003 | Gray | WO | WO 95/22318 | 8/1995 |
| 2003/0032935 A1 | 2/2003 | Damiano et al. | WO | WO 95/33553 | 12/1995 |
| 2003/0108614 A1 | 6/2003 | Volkonsky et al. | WO | WO 96/37165 | 11/1996 |
| 2003/0183962 A1 | 10/2003 | Buiser et al. | WO | WO 96/39464 | 12/1996 |
| 2003/0185895 A1 | 10/2003 | Lanphere et al. | WO | WO 98/04616 | 2/1998 |
| 2003/0185896 A1 | 10/2003 | Buiser et al. | WO | WO 98/10798 | 3/1998 |
| 2003/0187320 A1 | 10/2003 | Freyman | WO | WO 98/26737 | 6/1998 |
| 2003/0194390 A1 | 10/2003 | Krall et al. | WO | WO 98/47532 | 10/1998 |
| 2003/0203985 A1 | 10/2003 | Baldwin et al. | WO | WO 99/00187 | 1/1999 |
| 2003/0206864 A1 | 11/2003 | Mangin | WO | WO 99/12577 | 3/1999 |
| 2003/0215519 A1 | 11/2003 | Schwarz et al. | WO | WO 99/43380 | 9/1999 |
| 2003/0233150 A1 | 12/2003 | Bourne et al. | WO | WO 99/51278 | 10/1999 |
| 2004/0076582 A1 | 4/2004 | DiMatteo et al. | WO | WO 99/57176 | 11/1999 |
| 2004/0091543 A1 | 5/2004 | Bell et al. | WO | WO 00/23054 | 4/2000 |
| 2004/0092883 A1 | 5/2004 | Casey, III et al. | WO | WO 00/32112 | 6/2000 |
| 2004/0096662 A1 | 5/2004 | Lanphere et al. | WO | WO 00/40259 | 7/2000 |
| 2004/0101564 A1 | 5/2004 | Rioux et al. | WO | 00/66183 | 11/2000 |
| 2004/0186377 A1 | 9/2004 | Zhong et al. | WO | WO 00/71196 | 11/2000 |
| 2005/0025800 A1 | 2/2005 | Tan | WO | WO 00/74633 | 12/2000 |
| 2005/0226935 A1 | 10/2005 | Kamath et al. | WO | WO 01/12359 | 2/2001 |
| 2005/0238870 A1 | 10/2005 | Buiser et al. | WO | WO 01/66016 | 9/2001 |
| | | | WO | WO 01/70291 | 9/2001 |
| | FOREIGN PATENT DOCUMENTS | | WO | WO 01/72281 | 10/2001 |
| | | | WO | WO 01/76845 | 10/2001 |
| DE | 3834705 | 4/1990 | WO | WO 01/93920 | 12/2001 |
| DE | 94 14 868.6 | 12/1994 | WO | WO 02/11696 | 2/2002 |
| DE | 297 24 255 U1 | 10/2000 | WO | WO 02/34298 | 5/2002 |
| DE | 100 26 620 | 3/2002 | WO | WO 02/34299 | 5/2002 |
| EP | 0 067 459 | 12/1982 | WO | WO 02/34300 | 5/2002 |
| EP | 0 122 624 | 10/1984 | WO | 02/47731 | 6/2002 |
| EP | 0 123 235 | 10/1984 | WO | WO 02/43580 | 6/2002 |
| EP | 0 243 165 | 10/1987 | WO | WO 03/013552 | 2/2003 |
| EP | 0 294 206 | 12/1988 | WO | WO 03/016364 | 2/2003 |
| EP | 0 402 031 | 12/1990 | WO | WO 03/051451 | 6/2003 |
| EP | 0 422 258 | 4/1991 | WO | 03/084582 | 10/2003 |
| EP | 0 458 079 | 11/1991 | WO | WO 03/082359 | 10/2003 |
| EP | 0 458 745 | 11/1991 | WO | 2004/001446 | 12/2003 |
| EP | 0 470 569 | 2/1992 | WO | WO 2004/019999 | 3/2004 |
| EP | 0 547 530 | 6/1993 | WO | WO 2004/040972 | 5/2004 |
| EP | 0 600 529 | 6/1994 | WO | WO 2004/073688 | 9/2004 |
| EP | 0 623 012 | 11/1994 | WO | WO 2004/075989 | 9/2004 |
| EP | 0 706 376 | 4/1996 | | | |

WO 2005/057272 6/2005

OTHER PUBLICATIONS

"Pulmonary artery pseudoaneurysm/aneurysm," http://www.mamc.amedd.army.mil/williams/chest/vascular/paaneurysm/paaneyrysm.htm, 2 pages, site updated Feb. 20, 2002.

"Smart Sutures Tie Themselves", Apr. 26, 2002, http://www.sciam.com/article.cfm?articleID=00047706-121F-1CD0-B4A8809EC588, 2 pages.

Abbara et al., "Transcervical Expulsion of a Fibroid as a Result of Uterine Artery Embolization for Leiomyomata", JVIR, vol. 10, No. 4, pp. 409-411, 1999.

Abrahams, J.M. et al., "Delivery of Human Vascular Endothelial Growth Factor with Platinum Coils Enhances Wall Thickening and Coil Impregnation in a Rat Aneurysm Model", AJNR Am. J. Neuroradiol. 22:1410-1417, Aug. 2001.

Ahuja, A.A., "Platinum Coil Coatings to Increase Thrombogenicity: A Preliminary Study in Rabbits", AJNR Am. J. Neuroradiol. 14:794-798; Jul./Aug. 1993.

Antibody Labeling, http://www.altcorp.com/AffinityLabeling/ablaeling.htm, pp. 1-6, May 20, 2003.

Bachtsi, A.R. et al., "An Experimental Investigation of Enzyme Release from Poly(vinyl alcohol) crosslinked Microspheres", J. Microencapsulation, vol. 12, No. 1, pp. 23-35; 1995.

Barr, J.D., et al.,"polyvinyl Alcohol Foam Particles Sizes and Concentrations Injectable through Microcatheters", JVIR, vol. 9, No. 1, pp. 113-118; 1998.

Barton, P. et al., "Embolization of Bone Metastases", Journal of Vascular and Interventional Radiology, vol. 7, No. 1, Jan.-Feb. 1996, p. 81-88.

Barttinelli, L. et al., "New Class of Poly(vinyl alcohol) Polymrs as Column- Chromatography Stationary Phases for Candida Rugosa Lipase Isoforms Separation.", J. Chromatogr A, vol. 753, No. 1, pp. 47-55; 1996. Abstract. http://www.ncbi.nlm.nih.gov/entrez/query.fcgi?

Beaujeux, R. et al., "Trisacryl Gelatin Microspheres for Therapeutic Embolization, II: Preliminary Clinical Evaluation in Tumors and Arteriovenous Malformations," AJNR Am. J. Neuroradiol. 17:541-548, Mar. 1996.

Berenstein, A. et al., "Catheter and Material Selection for Transarterial Embolization: Technical Considerations. II. Materials.", Radiology, vol. 132, No. 3, pp. 631-639; 1979.

Berenstein, A. et al., "Microembolization Techniques of Vascular Occlusion: Radiologic, Patohologic, and Clinical Correlation", AJNR Am I Neuroradiol, vol. 2, No. 3, pp. 261-267; 1981. Abstract, http://www.ncbi.nlm.nih.gov/entrez/query.fcgi?

Berkowitz, R.P. et al., "Vaginal Expulsion of Submucosal Fibroids After Uterine Artery Embolization", Journal of Reproductive Medicine, vol. 44, No. 4, pp. 373-376; Apr. 1999 http://www.reproductivemedicine.com.

Bradley, E.A. et al., "Transcatheter Uterine Artery Embolisation to Treat Large Uterine Fibroids", British Journal of Obstetrics and Gynaecology, vol. 105, pp. 235-240; Feb. 1998.

Brockmann, J. et al., "Radiolabeling of p-Bz-DOTA-CD-11c antibody with [88]Y: Conjugation, Labeling, Biodistribution studies", 2 pages, 2000 http://www.kernchemie.uni-mainz.de/downloads/jb2000/b14_brockmann.pdf.

Bruix, J. et al., "Transarterial Embolization Versus Symptomatic Treatment in Patients With Advanced Hepatocellular Carcinoma: Results of a Randomized, Controlled Trial in a Single Institution", Hepatology, Jun. 1998, vol. 27, No. 6, pp. 1578-1583 Available Web Site: http://www.hepatitis-central.com/hcv/hcc/embolization/references.html.

Buhle, Jr. EL, "Re: Re: Hepatic Arterial Embolization", UCLA Medicine Online Available Web Site: http://www.meds.com/archive/mol-cancer/1996/msg00128.html.

Burczak, et al., "Long-term in vivo performance and biocompatibility of poly (vinyl alcohol) hydrogel macrocapsules for hybrid-type artificial pancreas", Biomaterials, vol. 17, No. 24, pp. 2351-2356, 1996, abs: http://www.ncbi.nlm.nih.gov/entrez/query.fcgi?cmd=retrieve&db=PubMed&list_uids=89824..., pp. 1, 2002.

Burczak, et al., "Polymeric materials for biomedical purposes obtained by radiation methods. V. hybrid artificial pancreas", Polim Med, vol. 24, No. 1-2, pp. 45-55, 1994, abs: http://www.ncbi.nlm.nih.gov/entrez/query.fcgi?cmd=retrieve&db=PubMed&list_uids=7915..., pp. 1, 2002.

Capozza et al., "Endoscopic treatment of vesico-ureteric reflux and urinary incontinence: technical problems in the paediatric patient," British Journal of Urology, 75(4):538-542 (Apr. 1995).

Carstensen, E.L. et al., "Determination of the Acoustic Properties of Blood and its Components", Journal of Acoustical Society of America, vol. 25, No. 2, pp. 286-289, Mar. 1953.

Choe, et al., "An experimental study of embolic effect according to infusion rate and concentration of suspension in transarterial particulate embolization", Invest Radiol, vol. 32, No. 5, pp. 260-270, 1997, abs: http://www.ncbi.nlm.nih.gov/entrez/query.fcgi?cmd=retrieve&db=PubMed&list_uids=9140745&dopt+Abs..., pp. 1, 2002.

Cirkel, U. et al., "Experience with Leuprorelin Acetate Depot in the Treatment of Fibroids: A German Multicentre Study", Clinical Therapeutics, vol. 14, Suppl. A, 1992.

Clarian Health Methodist—Indiana Lions Gamma Knife Center, "Arteriovenous Malformation, " http://www.clarian.com/tyhealth/gammaknife/cond_arter.asp, 4 pages, Last Updated on Mar. 20, 2000.

Colombo M, "Treatment of Hepatocellular Carcinoma", University of Milan, Inst Internal Med, Irccs Maggiore Res Unit Liver, Canc, Firc, Via Pace 9 1-20122 Milan, Italy Source: Journal of Viral Hepatitis, 1997;4:125-130 Available Web Site: http://home.texoma.net/~moreland/stats/hec-9.html. Concentric Medical, Inc.—Product Information (3 pages), 2002.

Cruise et al., "In Vitro and In Vivo Characterization of a Hydrogel-Based Aneurysm Embolization System," Society for Biomaterials 28th Annual Meeting Transactions, p. 203 (2002).

Deasy, P. B., "Microencapsulation and Related Drug Processes", New York, NY, Marcel Dekker, Inc., 345 pages, 1984 (Table of Contents only).

DeGast, A.N. et al., "Transforming Growth Factor β-coated Platinum Coils for Endovascular Treatment of Aneurysms: An Animal Study", Neurosurgery, vol. 49, No. 3, pp. 690-696, Sep. 2001.

Derdeyn, et al., "Collagen-coated acrylic characteristics for embolotherapy: in vivo and In vitro characteristics", American Journal of Neuroradiology, vol. 18, No. 4, pp. 647-653, 1997, abs: http://www.ncbi.nlm.nih.gov/entrez/query.fcgi?cmd=retrieve&db=PubMed&list_uids=9127025&dopt=Abs..., pp. 1, 2002.

Derdeyn, et al., "Polyvinyl alcohol particle size and suspension characteristics", American Journal of Neuroradiology, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, Jan. 1994, vol. 83, No. 1, pp. 104-106.

Duckwiler et al., "Catheters, embolic agents spark neurointervention," Diagnostic Imaging, 16(5):66-72 (May 1994).

Eskridge, "Interventional Neuroradiology," Radiology, 172:991-1006 (Nov. 1989).

Feldman, L. et al., "Transcatheter Vessel Occlusion: Angiographic Results Versus Clinical Success", Radiology, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

Fritzsch, T. et al., "SH U 508, A Transpulmonary Echocontrast Agent", Investigative Radiology, vol. 25, Supplement 1, pp. S160-S161, Sep. 1990.

Fujimoto, S. et al., "Biodegradable Mitomycin C Microspheres Given Intra-Arterially for Inoperable Hepatic Cancer", Cancer, vol. 56, pp. 2404-2410, 1985.

Gander, et al., "Effect of polymeric network structure on drug release from cross-linked poly(vinyl alcohol) micromatrices", Pharm Res, vol. 6, No. 7, pp. 578-584, 1989, abs: http://www.ncbi.nlm.nih.gov/entrez/query.fcgi?cmd=retrieve&db=PubMed&lst_uids=25080..., pp. 1, 2002.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992, abs: http://www.ncbi.nlm.nih.gov/entrez/query.fcgi?cmd=retrieve&db=PubMed&list_uids=15452 . . . , pp. 1, 2002.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244-1255.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999, abs: http://www.ncbi.nlm.nih.gov/entrez/query.fcgi?cmd=retrieve&db=PubMed&list_uids=10065360&dop=A . . . , pp. 1, 2002.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material",*J Biomed Mater Res*, vol. 26, No. 4, pp. 467-479, 1992, abs: http://www.ncbi.nlm.nih.gov/entrez/query.fcgi?cmd=retrieve&db=PubMed&list_uids=1601900&dopt=Abs . . . , pp. 1, 2002.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Hamada, et al., "Embolization with cellulose porous beads, II: Clinical Trial", abs: http://www.ajnr.org/content/abstract/17/10/1901?ijkey=R.a2vRMiet1Xw, pp. 1-2, 2002.

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Horak, et al., "Hydrogels in endovascular embolization. II. Clinical use of spherical particles", *Biomaterials*, vol. 7, 1986.

Huang, et al., "Percutaneous endovascular embolization of intracerebral arteriovenous malformations. Experience in 72 cases", *Chin Med J*,vol. 108, No. 6, pp. 413-419, 1995, abs: http://www.ncbi.nlm.nih.gov/entrez/query.fcgi?cmd=retrieve&db=PubMed&list_uids=75552 . . . , pp. 1, 2002.

Jack, et al., "Radiolabeled polyvinyl alcohol particles: a potential agent to monitor embolization procedures", *Int J Rad Appl Instrum B*, vol. 13, No. 3, pp. 235-243, 1986, abs: http://www.ncbi.nlm.nih.gov/entrez/query.fcgi?cmd=retrieve&db=PubMed&list_uids=37712, pp. 1, 2002.

Jiaqi, Y. et al., "A New Embolic Material: Super Absorbent Polymer (SAP) Microsphere and Its Embolic Effects", *Nippon Acta Radiologica* 1996 (56):19-24.

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Kai, et al., "The utility of the microcrystalline cellulose sphere as a particulate embolic agent: an experimental study", *American Journal of Radiology*, vol. 21, No. 6, pp. 1160-1163, 2000, or http://www.ajnr.org/cgi/content/full/21/6/1160, pp. 1-7, 2002.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, Jun. 1978, vol. 130, pp. 1193-1194.

Kerber, "Flow-Controlled Therapeutic Embolization: A Physiologic and Safe Technique", *AJR*, Mar. 1980, vol. 134, pp. 557-561.

Kerber, C., "Balloon Catheter with a Calibrated Leak", *Radiology*, vol. 120, pp. 547-550, Sep. 1976.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim et al., "Hollow Silica Spheres of Controlled Size and Porosity by Sol-Gel Processing," *J. Am. Ceram. Soc.*, 74(8):1987-1992 (Aug. 1991).

Kim, et al., "Composite poly(vinyl alcohol) beads for controlled drug delivery", *Pharm Res*, vol. 9. No. 1, pp. 10-16, 1992, abs: http://www.ncbi.nlm.nih.gov/entrez/query.fcgi?cmd=retrieve&db=PubMed&list_uids=1589392&dopt=Abs . . . , pp. 1, 2002.

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20 No. 4, pp. 367-373, 1992, abs: http://www.ncbi.nlm.nih.gov/entrez/query.fcgi?cmd=retrieve&db=PubMed&list_uids=1570057&dopt=Abs . . . , pp. 1, 2002.

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp.

Kurosaki et al., "Evaluation of PVA-Gel Spheres as GI-Transit Time Controlling Oral Drug Delivery System", *Proceedings of the 19th International Symposium on Controlled Release of Bioactive Materials*, Jul. 26-31, 1992, Orlando, Florida, pp. 273-274.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987, abs: http://www.ncbi.nlm.nih.gov/entrez/query.fcgi?cmd=retrieve&db=PubMed&list_uids=34963 . . . , pp. 1, 2002.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983, abs: http://www.ncbi.nlm.nih.gov/entrez/query.fcgi?cmd=retrieve&db=PubMed&list_uids=6823530&dop=Abs . . . , pp. 1, 2002.

Latchaw et al., "Polyvinyl Foam Embolization of Vascular and Neoplastic Lesions of the Head, Neck, and Spine", *Radiology*, Jun. 1979, vol. 131, pp. 669-679.

Laurent, "Materials and biomaterials for interventional radiology," *Biomed. & Pharmacother.*, 52:76-88 (1998).

Lemperle et al., "PMMA Microspheres for Intradermal Implantation: Part I. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, Mar. 2001, vol. 12, No. 3, pp. 320-326.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).
Lipman, "Uterine artery embolization for the treatment of symptomatic uterine fibroids: A review," *Applied Radiology*, 29(7):15-20 (Jul. 2000).
Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.
Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.
Markoff, et al., "Uterine arteriovenous malformation successfully embolized with a liquid polymer, isobutyl 2-cyanoacrylate", pp. 659-660, 1999.
Markoff, et al., "Uterine arteriovenous malformation successfully embolized with a liquid polymer, isobutyl 2-cyanoacrylate", *Am. J Obstet. Gynecol.*, 155:659-660 (Sep. 1986).
Markus, H.S., "Experimental Aspects of High-Intensity Transient Signals in the Detection of Emboli," *J Clin Ultrasound* 23:81-87 (1995).
Maruhashi, "Modified Polyvinyl Alcohols I and II," *Plyvinyl Alcohol—Developments*, John Wiley & Sons, Chichester, England, pp. 160-161 and pp. 186-191 (1992).
Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.
Matsumaru, et al., "Embolic materials for endovascular treatment of cerebral lesions", *J Biomater Sci Polym Ed*, vol. 8, No. 7, pp. 555-569, 1997, abs: http://www.ncbi.nlm.nih.gov/entrez/query.fcgi?cmd=retrieve&db=PubMed&list_uids=91953 . . . , pp. 1, 2002.
Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.
Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.
Mavligit, G. et al., "Gastrointestinal Leiomyosarcoma Metastatic to the Liver", *Cancer*, vol. 75, No. 8, Apr. 15, 1995, pp. 2083-2088.
McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.
MerocelXL Sponge with Hytrol http://www.xomed.com/newproducts/merocelxl/merocelxl_earwick.asp, 3 pages, 2001.
Moroz, P. et al., "Arterial Embolization Hyperthermia in Porcine Renal Tissue", *Journal of Surgical Research*, vol. 105, No. 2, pp. 209-214, Jun. 15, 2002.
Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.
Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997, abs: http://www.ncbi.nlm.nih.gov/entrez/query.fcgi?cmd=retrieve&db=PubMed&list_uids=909004 . . . , pp. 1, 2002.
Nakstad, et al., "Embolization of intracranial arteriovenous malformations and fistulas with polyvinyl alcohol particles nad platinum fibre coils", *Neuroradiology*, vol. 34, No. 4, pp. 348-351, 1992, abs: http://www.ncbi.nlm.nih.gov/entrez/query.fcgi?cmd=retrieve&db=PubMed&list_uids=15284 . . . , pp. 1, 2002.
Namiki, "Application of Teflon Paste for Urinary Incontinence—Report of 2 Cases," *Uro. Int.*, 39:280-282 (1984).
Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997, abs: http://www.ncbi.nlm.nih.gov/entrez/query.fcgi?cmd=retrieve&db=PubMed&list_uids=92860 . . . , pp. 1, 2002.
Nikishin LF et al., 1999, "Interventional radiology in diffuse toxic goiter", *European Congress of Radiology—ECR 1999* Available Web Site: http://www.ecr.org/conferences/ecr1999/sciprg/abs/p090041.htm.
Ophir, et al., "Ultrasonic backscatter from contrast producing collagen microspheres", *Ultrasonic Imaging*, vol. 2, pp. 67-77, 1980.
Orsini, L. F. et al., "Pelvic Organs in Premenarcheal Girls: Real-Time Ultrasonography", *Radiology*, vol. 153, No. 1, pp. 113-116, Oct. 1984.
Parker, et al., "A particulate contrast agent with potential for ultrasound imaging of liver", *Ultrasound in Medicine and Biology*, vol. 13, No. 9, pp. 555-566, 1987.
Pesant A.C. et al., 1997, "Dural fistulas involving the cavernous sinus: Treatment by embolization—7 cases", *European Congress of Radiology—ECR 1997* Available Web Site: http://www.ecr.org/conferences/ecr1997/sciprg/abs/9703088p.htm.
Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.
Politano et al., "Periurethral Teflon Injection for Urinary Incontinence," *The Journal of Urology*, 111:180-183 (1974).
Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.
Progelhof et al., "Table 4.21. Properties of electrical insulating films (101)," *Polymer Engineering Principles: Properties, Processes, and Tests for Design*, Hanser Publishers, Munich, p. 383 (1993).
Purdy, et al., "Arteriovenous malformations of the brain: choosing embolic materials to enhance safety and ease of excision", *J Neurosurg*, vol. 77, No. 2, pp. 217-222, 1992, abs: http://www.ncbi.nlm.nih.gov/entrez/query.fcgi?cmd=retrieve&db=PubMed&list_=uids=16250 . . . , pp. 1, 2002.
Quisling, et al., "Histopathology analysis of intraarterial polyvinyl alcohol microemboli in rat cerebral cortex", *American Journal of Neuroradiology*, vol. 5, pp. 101-104, 1984.
Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, Feb. 2001, vol. 12, No. 2, pp. 187-193.
Ramos, et al., "Tumor vascular signals in renal masses: detection with Doppler US", *Radiology*, vol. 168, No. 3, pp. 633-637, 1988.
Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).
Ravina, J.H. et al., "Arterial Embolisation to Treat Uterine Myomata", *Lancet*, vol. 346, pp. 671-674, Sep. 9, 1995.
Repa, I. et al., "Mortalities Associated with Use of a Commercial Suspension of Polyvinyl Alcohol", *Radiology* 1989; 170:395-399.
Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).
Rump, A. et al., "Pharmacokinetics of Intraarterial Mitomycin C in the Chemoembolisation Treatment of Liver Metastases", *Gen. Pharmac.* vol. 27, No. 4, pp. 669-671, 1996.
Schetky, "Shape-Memory Alloys," *Encyclopedia of Chemical Technology*, Third Edition, vol. 20, John Wiley & Sons, New York, pp. 726-736 (1982).
Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).
Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.
Schwarz, K.Q., "The Acoustic Filter: An Ultrasonic Blood Filter for the Heart-Lung Machine," *Journal of Thoracic and Cardiovascular Surgery* 104(6):1647-1653 (1992).

Shafik, "Intraesophageal Polytef injection for the treatment of reflux esophagitis," *Surg. Endosc.*, 10:329-331 (1996).

Shafik, A., "Intraesophageal Polytef injection for the treatment of reflux esophagitis", *Department of Surgery and Experimental Research, Faculty of Medicine, Cairo University*, Cairo, Egypt, pp. 1-2, Received: Jun. 22, 1994; Accepted: Oct. 15, 1994 http://www.ahmedshafik.org/Group-D/d016.htm.

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Skotland, T. et al., "In Vitro Stability Analyses as a Model for Metabolism of Ferromagnetic Particles (Clariscan3), a Contrast Agent for Magnetic Resonance Imaging", J. Pharm. Biomed. Anal., vol. 28, No. 2, pp. 323-329 (2002).

Smith et al., "Evaluation of Polydimethylsiloxane as an alternative in the Endoscopic Treatment of Vesicoureteral Reflux," *The Journal of Urology*, 152:1221-1224 (Oct. 1994).

Smith, M.D. et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Spickler, et al., "The MR appearance of endovascular embolic agents in vitro with clinical correlation", *Comput Med Imaging Graph*, vol. 14, No. 6, pp. 415-723, 1990, abs: http://www.ncbi.nlm.nih.gov/entrez/query.fcgi?cmd=retrieve&db=PubMed&list_uids=21487..., pp. 1, 2002.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al., "Collateral Circulation Following Repeated Distal Embolization of the Hepatic Artery in Pigs," *Invest Radiol* 1984;19:179-183.

Strunk, et al., "Treatment of congenital coronary arteriovenous malformations with microparticle embolization", *Cathet Cardiovasc Diagn*, vol. 22, No. 2, pp. 133-136, 1991, abs: http://www.ncbi.nlm.nih.gov/entrez/query.fcgi?cmd=retrieve&db=PubMed&list_uids=2009563&dop=Abs ..., pp. 1, 2002.

Swanson DA et al., 1980, "The role of embolization and nephrectomy in the treatment of metastatic renal carcinoma", Urologic Clinics of North America 7(3):719-730, 1980. University of Pennsylvania Cancer Center— Oncolink. Available Web Site: http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1-3, pp. 123-133.

Tadavarthy et al., "Polyvinyl Alcohol (Ivalon) as an Embolizing Agent", *The American Journal of Roentgenology Radium Therapy and Nuclear Medicine*, Nov. 1975, vol. 125, No. 3, pp. 609-616.

Tadavarthy et al., "Polyvinyl Alcohol (Ivalon) as an Embolizing Agent", *Seminars in Interventional Radiology*, vol. 1, No. 2, Department of Radiology, University of Minnesota Hospitals, Minneapolis, Minnesota, Jun. 1984, pp. 101-109.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tao, et al., "Study of microspheres for embolization of the hepatic artery", *Yao Xue Xue Bao*, vol. 23, No. 1, pp. 55-60, 1988, abs: http://www.ncbi.nlm.nih.gov/entrez/query.fcgi?cmd=retrieve&db=PubMed&list_uids=3400477&dop=A, pp. 1, 2002.

Tao, et al., "Study on embolization of hepatitic artery using microspheres", Acta Pharmaceutica Sinica vol. 23, No. 1, pp. 55-60; 1988. Translation.

Terada, et al., "Preoperative embolization of meningiomas fed by ophthalmic branch arteries", *Surg Neurol*, vol. 45, No. 2, pp. 161-166, 1996, abs: http://www.ncbi.nlm.nih.gov/entrez/query.fcgi?cmd=retrieve&db=PubMed&list_uids=86070..., pp. 1, 2002.

Thanoo, B. C. et al., "Preparation and Properties of Barium Sulphate and Methyl Iothalamate Loaded Poly(vinyl Alcohol) Microspheres as Radiopaque Particulate Emboli", *Journal of Applied Biomaterials*, vol. 2, 67-72 (1991).

Thanoo, et al., "Controlled release of oral drugs from cross-linked polyvinyl alcohol microspheres", *J Pharm Pharmacol*, vol. 45, No. 1, pp. 16-20, 1993, abs: http://www.ncbi.nlm.nih.gov/entrez/query.fcgi?cmd=retrieve&db=PubMed&list_uids=8094438&dop=Abs..., pp. 1, 2002.

Thanoo, et al., "Tantalum loaded silicone micropsheres as particulate emboli", *J Microencapsul*, vol. 8, No. 1, pp. 95-101, 1991, abs: http://www.ncbi.nlm.nih.gov/entrez/query.fcgi?cmd=retrieve&db=PubMed&list_uides=1880697&dop=Abs... pp. 1, 2002.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976.

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156. 1994, abs: http://www.ncbi.nlm.nih.gov/entrez/query.fcgi?cmd=retrieve&db=PubMed&list_uids=80912..., pp. 1, 2002.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 1998, Feb;21(2):88-9 Available Web Site: http://www.doyma.es/copiani/revistas/gastro/abstr/abs_p080.html.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2002.

Walsh RM et al., "Role of Angiography and Embolization for Acute Massive Upper Gastronintestinal Hemorrhage," *J. Gastrointest. Surg.*, 3:61-66 (1999).

Walsh RM et al., 1998, "Role of Angiography and Embolization for Acute Massive Upper Gastronintestinal Hemorrhage." Department of General Surgery and Radiology, Cleveland Clinic Foundation, Cleveland, Ohio. Available Web Site: http://www.ssat.com/98ddw/abstscorrt-47.html.

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Wikholm G et al., 1996, "Embolization of Cerebral Arteriovenous Malformations: Part I—Technique, Morphology, and Complications", Departments of Neurology (CL) and Interventional Radiology (GW, PS), Sahlgrenska University Hospital, Goteborg, Sweden. Neurosurgery. Sep, 1996;39(3):448-57; discussion 457-9. Available Web Site: http://www.wwilkins.com/neurosurgery/0148-396X9-96inter.html.

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, 1999, "Interventionalists offer management option for uterine fibroids." Diagnostic Imaging, pp. 47-49. Available Web Site: http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology* 142:351-354, Feb. 1982.

Wu, A.M., "Engineered Antibodies for Breast Cancer Imaging and Therapy," http://www.cbcrp,org/ research/PageGrant.asp?grant_id=111, 3 pages, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," Asian J. Surg. 18(2): 122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou , Ying-hua, et al. "Experimental Canine Hapatic Artery Embolization with Polyvinyl Alcohol Microspheres", *Zhong Hua Fang-She Xue ZaZhi*, Dec. 23, 1989 (6):330-332.

Zou , Ying-hua, et al. "Experimental Canine Hapatic Artery Embolization with Polyvinyl Alcohol Microspheres" (Translation), *Zhong Hua Fang-She Xue ZaZhi*, Dec. 23, 1989 (6):330-332.

\* cited by examiner

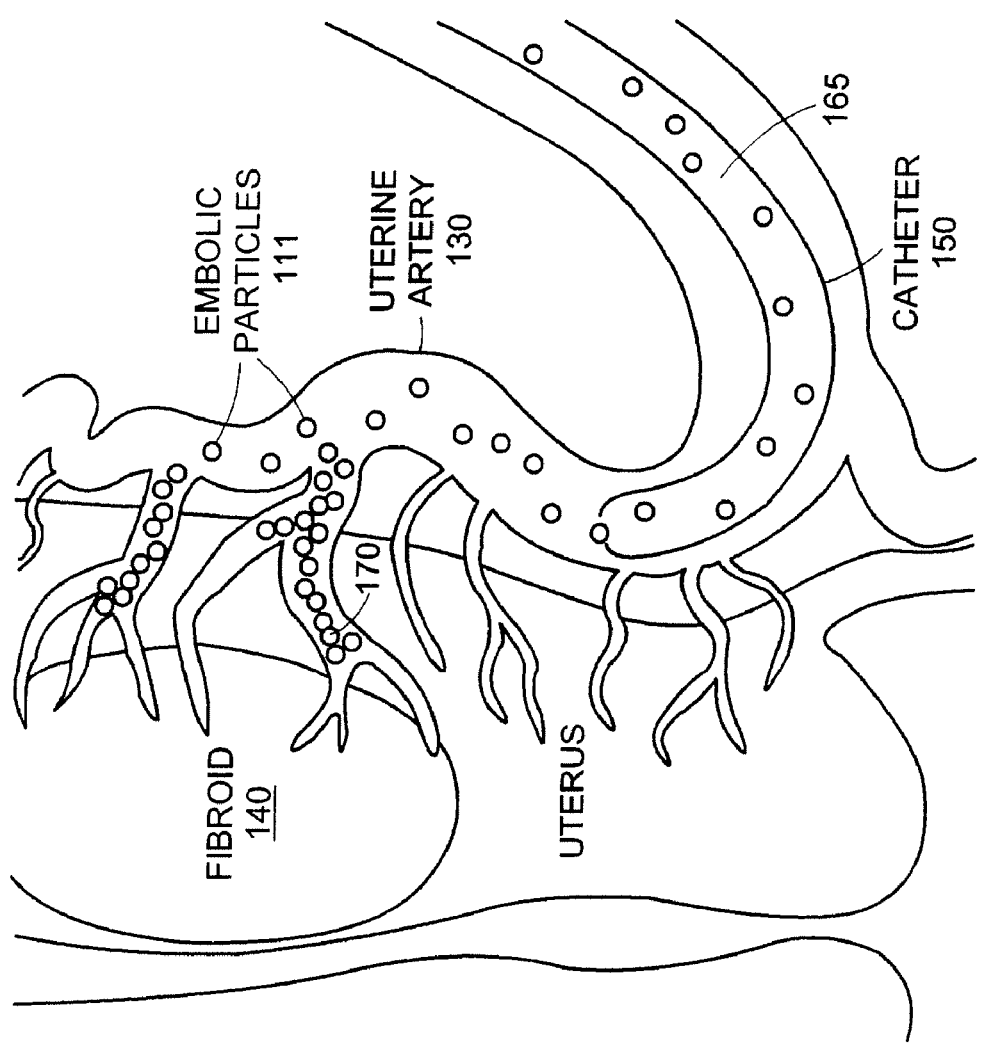

POROUS POLYMERIC PARTICLE COMPRISING POLYVINYL ALCOHOL AND HAVING INTERIOR TO SURFACE POROSITY-GRADIENT

CROSS-REFERENCE TO RELATED APPLICATIONS

This application is a continuation of and claims priority under 35 U.S.C. §120 to U.S. patent application Ser. No. 10/637,130, filed Aug. 8, 2003, now U.S. Pat. No. 7,449,236, the entire contents of which are hereby incorporated by reference. The entire contents of both U.S. Ser. No. 10/215,594, filed Aug. 9, 2002, now U.S. Pat. No. 7,588,780, and U.S. Ser. No. 10/615,276, filed Jul. 8, 2003, now abandoned, are hereby incorporated by reference.

TECHNICAL FIELD

The invention relates to embolization.

BACKGROUND

Therapeutic vascular occlusions (embolizations) are used to prevent or treat pathological conditions in situ. Compositions including embolic particles are used for occluding vessels in a variety of medical applications. Delivery of embolic particles through a catheter is dependent on size uniformity, density and compressibility of the embolic particles.

SUMMARY

In one aspect, the invention features a polymeric particle having a diameter of about 500 microns or less. The particle has a first density of pores in an interior region and a second density of pores at a surface region. The first density is different from the second density.

In another aspect, the invention features a polymeric particle having a diameter of about 500 microns or less. The particle has a first average pore size in an interior region and a second average pore size at the surface region. The first average pore size is different from the second average pore size.

In a further aspect, the invention features a composition that includes a plurality of particles in a carrier fluid. At least some of the plurality of particles have a diameter of about 500 microns or less. At least some of the particles having a diameter of about 500 microns or less have a first density of pores in an interior region and a second density of pores at a surface region. The first density is different from the second density.

In one aspect, the invention features a composition that includes a plurality of particles in a carrier fluid. At least some of the plurality of particles have a diameter of about 500 microns or less. At least some of the particles having a diameter of about 500 microns or less have a first average pore size in an interior region and a second average pore size at a surface region. The first average pore size is different from the second average pore size.

In another aspect, the invention features a method that includes passing a solution that contains a base polymer and a gelling precursor through an orifice having a diameter of about 200 microns or less (e.g., about 100 microns or less, about 10 microns or more) to form drops containing the base polymer and the gelling precursor. The method also includes forming particles containing the base polymer and the gelling precursor from the drops containing the base polymer and the gelling precursor.

In a further aspect, the invention features a method that includes heating a solution that contains a base polymer and a gelling precursor to a temperature of at least about 50° C. (e.g., about 65° C. or more, about 75° C. or more, about 85° C. or more, about 95° C. or more, about 105° C. or more, about 115° C. or more, about 121° C.). The method also include forming particles containing the base polymer and the gelling precursor from the solution containing the base polymer and the gelling precursor.

In one aspect, the invention features a method that includes passing a solution containing a base polymer and a gelling precursor through an orifice while vibrating the orifice at a frequency of about 0.1 KHz or more (e.g., about 0.8 KHz or more, about 1.5 KHz or more) to form drops containing the base polymer and the gelling precursor. The method also includes forming particles containing the base polymer and the gelling precursor from the drops containing the base polymer and the gelling precursor.

In another aspect, the invention features a method that includes forming drops containing the base polymer and the gelling precursor, and contacting the drops with a gelling agent to form particles containing the base polymer and the gelling precursor. The gelling agent is at a temperature greater than room temperature (e.g., a temperature of about 30° C. or more).

In a further aspect, the invention features a method that includes forming drops containing a base polymer and a gelling precursor, and contacting the drops with a gelling agent to form particles containing the base polymer and the gelling precursor. The gelling agent is contained in a vessel, and the method further includes bubbling a gas through the gelling agent, disposing a mist containing the gelling agent between a source of the drops and the vessel, including a surfactant in the mixture containing the gelling agent, and/or stirring the gelling agent.

In one aspect, the invention features a method that includes administering to a subject a therapeutically effective amount of a composition including a plurality of particles in a carrier fluid. At least some of the plurality of particles have a diameter of about 500 microns or less. At least some of the particles having a diameter of about 500 microns or less have a first density of pores in an interior region and a second density of pores at a surface region. The first density is different from the second density.

In another aspect, the invention features a method that includes administering to a subject a therapeutically effective amount of a composition including a plurality of particles in a carrier fluid. At least some of the plurality of particles have a diameter of about 500 microns or less. At least some of the particles having a diameter of about 500 microns or less have a first average pore size in an interior region and a second average pore size at a surface region. The first average pore size is different from the second average pore size.

Embodiments may also include one or more of the following.

The first density can be greater than the second density.

The first average pore size can be greater than the second average pore size.

A particle can have a diameter of about 10 microns or more. A particle can have a diameter of about 100 microns or more and/or a diameter of about 300 microns or less. A particle can have a diameter of about 300 microns or more.

A particle can include at least one polymer selected from polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, and poly(lactic-co-glycolic) acids.

A particle can be at least partially coated with a substantially bioabsorbable material.

A particle can have a density of from about 1.1 grams per cubic centimeter to about 1.4 grams per cubic centimeter.

A particle can have a sphericity of about 0.9 or more.

After compression to about 50 percent, a particle has a sphericity of about 0.9 or more.

A particle can include about 2.5 weight percent or less polysaccharide (e.g., alginate). An alginate can have a guluronic acid content of about 60 percent or greater.

A particle can be substantially insoluble in DMSO.

A particle can be substantially free of animal-derived compounds.

A carrier fluid can include a saline solution, a contrast agent or both.

A plurality of particles can have a mean diameter of about 500 microns or less and/or about 10 microns or more. A plurality of particles can have a mean diameter of about 100 microns or more and/or a mean diameter of about 300 microns or less. A plurality of particles can have a mean diameter of about 300 microns or more.

A method can include heating the solution to a temperature of at least about 50° C. before passing the solution through the orifice.

A method can include vibrating the nozzle orifice at a frequency of at least about 0.1 KHz as the solution passes therethrough.

A method can further include contacting the drops with a gelling agent to gel the gelling precursor to form particles comprising the base polymer and gelled gelling precursor.

A method can further include removing at least some of the gelled gelling precursor from the particles.

A composition can be administered by percutaneous injection.

A composition can be administered by a catheter.

A composition can be introduced into the subject using a lumen having a diameter that is smaller than a mean diameter of the plurality of particles.

A composition can be used to treat a cancer condition. The cancer condition can be, for example, ovarian cancer, colorectal cancer, thyroid cancer, gastrointestinal cancer, breast cancer, prostate cancer and/or lung cancer. Treating the cancer condition can include at least partially occluding a lumen providing nutrients to a site of the cancer condition with at least some of the plurality of particles.

A method can include at least partially occluding a lumen in the subject with at least some of a plurality of particles.

Embodiments of the invention may have one or more of the following advantages. Some disorders or physiological conditions can be mediated by delivery of embolic compositions. Embolic compositions can be used, for example, in treatment of fibroids, tumors (e.g., hypervascular tumors), internal bleeding, and/or arteriovenous malformations (AVMs). Examples of fibroids can include uterine fibroids which grow within the uterine wall, on the outside of the uterus, inside the uterine cavity, between the layers of broad ligament supporting the uterus, attached to another organ or on a mushroom-like stalk. Internal bleeding includes gastrointestinal, urinary, renal and varicose bleeding. AVMs are, for example, abnormal collections of blood vessels which shunt blood from a high pressure artery to a low pressure vein. The result can be hypoxia and malnutrition of those regions from which the blood is diverted.

Spherical embolic particles in the embolic compositions can be tailored to a particular application by, for example, varying particle size, porosity gradient, compressibility, sphericity and density of the particles. In embodiments in which the spherical embolic particles have a substantially uniform size, the particles can, for example, fit through the aperture of a catheter for administration by injection to a target site, without partially or completely plugging the lumen of the catheter. The spherical embolic particles have a mean diameter of about 1200 microns or less (e.g., from about 100 microns to about 500 microns). Size uniformity of ±15 percent of the spherical embolic particles allows the particles to stack evenly in the cylindrical lumen of the blood vessel to completely occlude the blood vessel lumen. Suspensions containing the embolic particles at a density of about 1.1 grams per cubic centimeter to about 1.4 grams per cubic centimeter can be prepared in calibrated concentrations of the embolic particles for ease of delivery by the physician without rapid settlement of the suspension. Control in sphericity and uniformity of the embolic particles can result in reduction in aggregation caused, for example, by surface interaction of the particles. In addition, the embolic particles are relatively inert in nature.

Features and advantages are in the description, drawings, and claims.

DESCRIPTION OF DRAWINGS

FIG. 1A is a schematic illustrating injection of an embolic composition including embolic particles into a vessel, while FIG. 1B is an enlarged view of the region 1B in FIG. 1A;

FIG. 2A is a light micrograph of a collection of hydrated embolic particles, while

FIG. 3A is a schematic of the manufacture of an embolic composition while

DETAILED DESCRIPTION

Composition

Figure 1A:
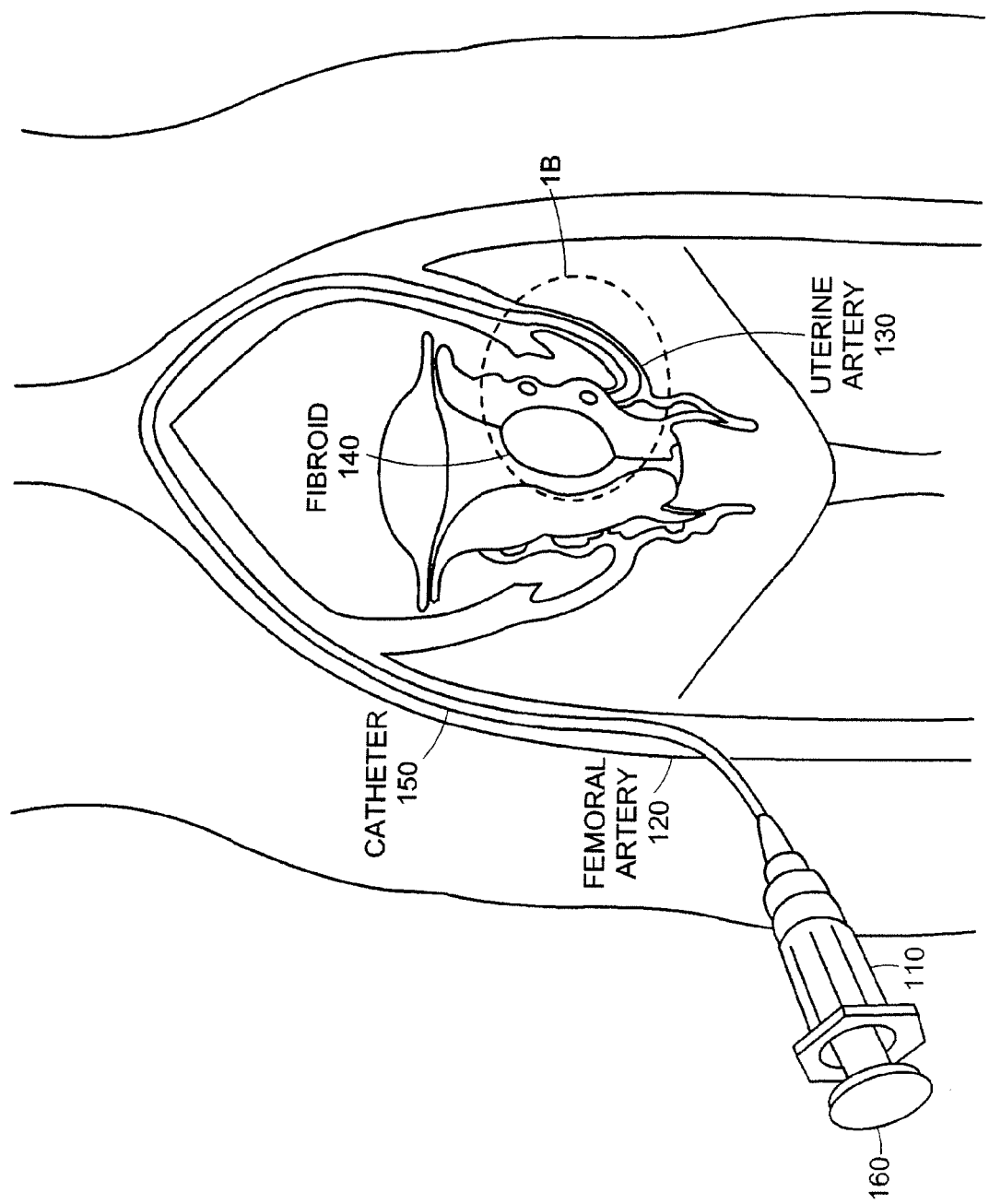

Referring to FIGS. 1A and 1B, an embolic composition, including embolic particles 111 and a carrier fluid, is injected into a vessel through an instrument such as a catheter 150. Catheter 150 is connected to a syringe barrel 110 with a plunger 160. Catheter 150 is inserted, for example, into a femoral artery 120 of a patient. Catheter 150 delivers the embolic composition to, for example, occlude a uterine artery 130 leading to a fibroid 140. Fibroid 140 is located in the uterus of a female patient. The embolic composition is initially loaded into syringe 110. Plunger 160 of syringe 110 is then compressed to deliver the embolic composition through catheter 150 into a lumen 165 of uterine artery 130.

Referring particularly to FIG. 1B which is an enlarged view of section 1B of FIG. 1A, uterine artery 130 is subdivided into smaller uterine vessels 170 (e.g., having a diameter of about 2 millimeters or less) which feed fibroid 140. The embolic particles 111 in the embolic composition partially or totally fill the lumen of uterine artery 130, either partially or completely occluding the lumen of the uterine artery 130 that feeds uterine fibroid 140.

In general, the particles are substantially formed of a polymer, such as a highly water insoluble, high molecular weight polymer. An example of such a polymer is a high molecular weight polyvinyl alcohol (PVA) that has been acetalized. The embolic particles can be substantially pure intrachain 1,3-acetalized PVA and substantially free of animal derived residue such as collagen. In embodiments, the particles include a minor amount (e.g., about 2.5 weight percent or less, about one weight percent or less, about 0.2 weight percent or less) of a gelling material (e.g., a polysaccharide, such as alginate).

Figure 2A:
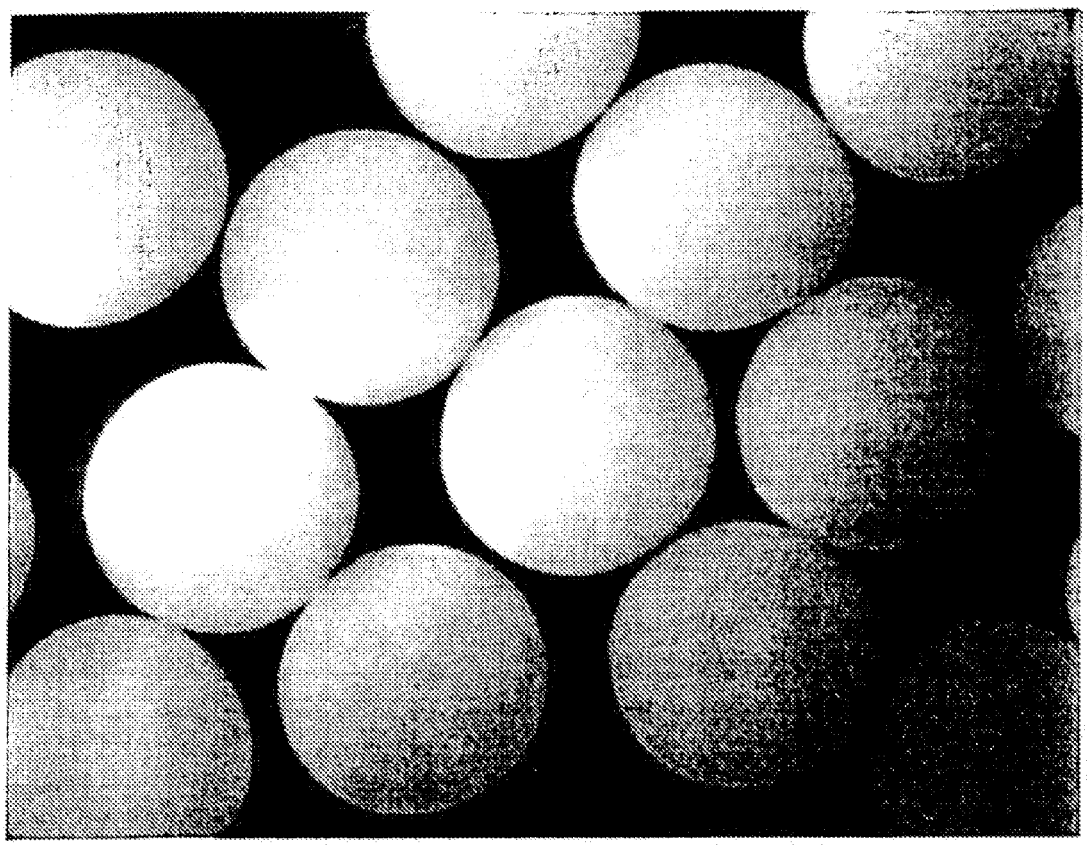
Figure 2B:
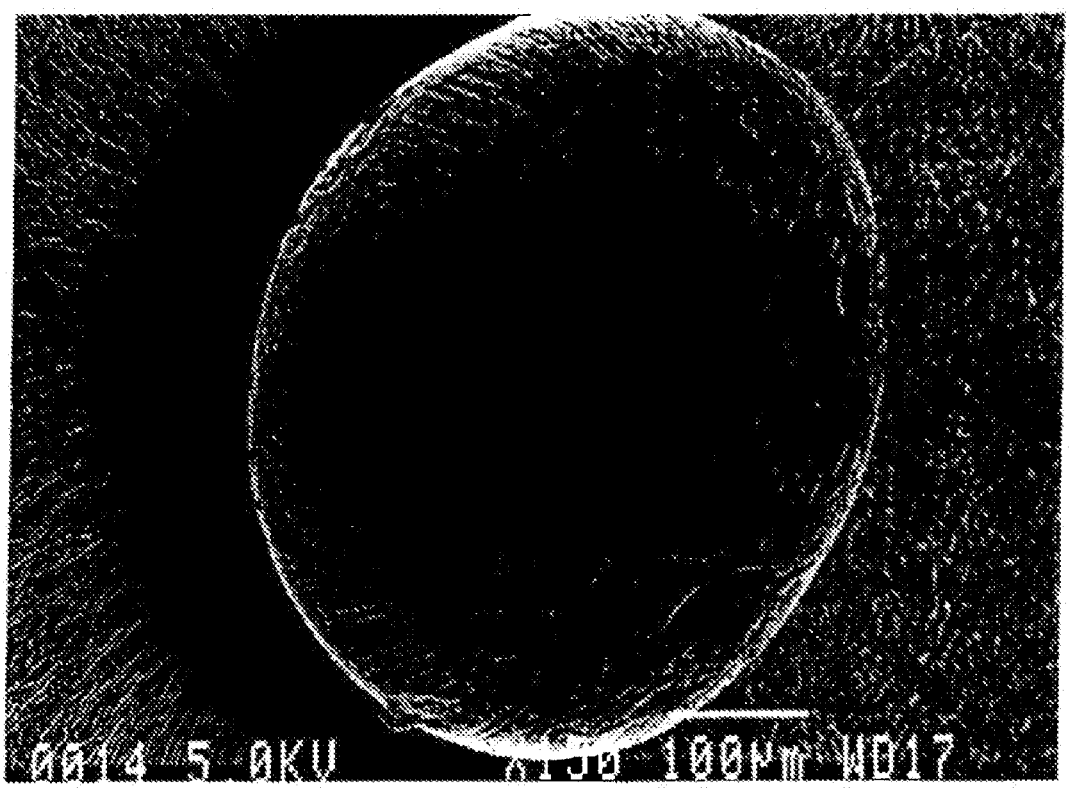
FIG. 2B is a scanning electron microscope (SEM) photograph of an embolic particle surface and FIGS. 2C-2E are cross-sections of embolic particles.
Figure 2C:
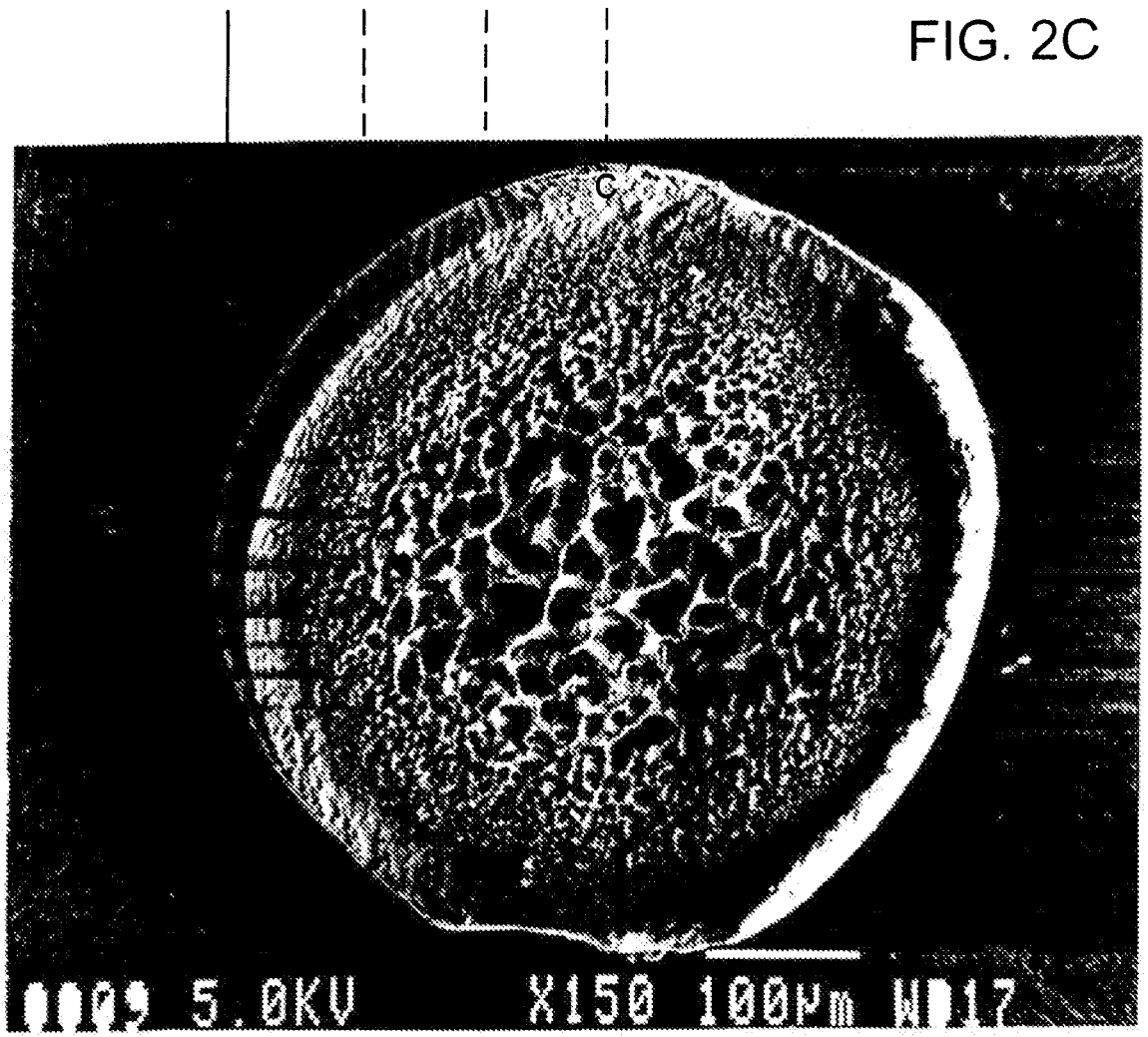
Figure 2D:
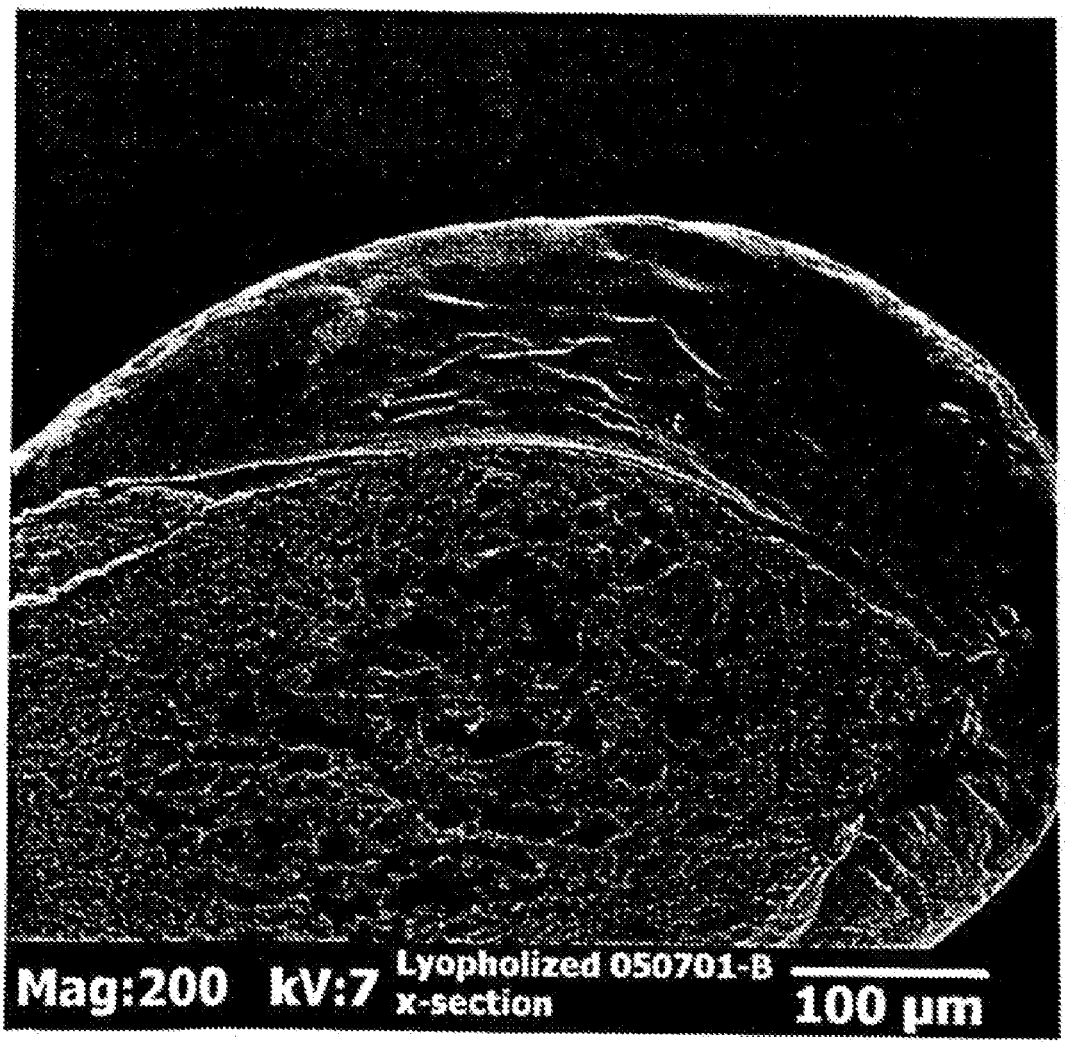
Figure 2E:
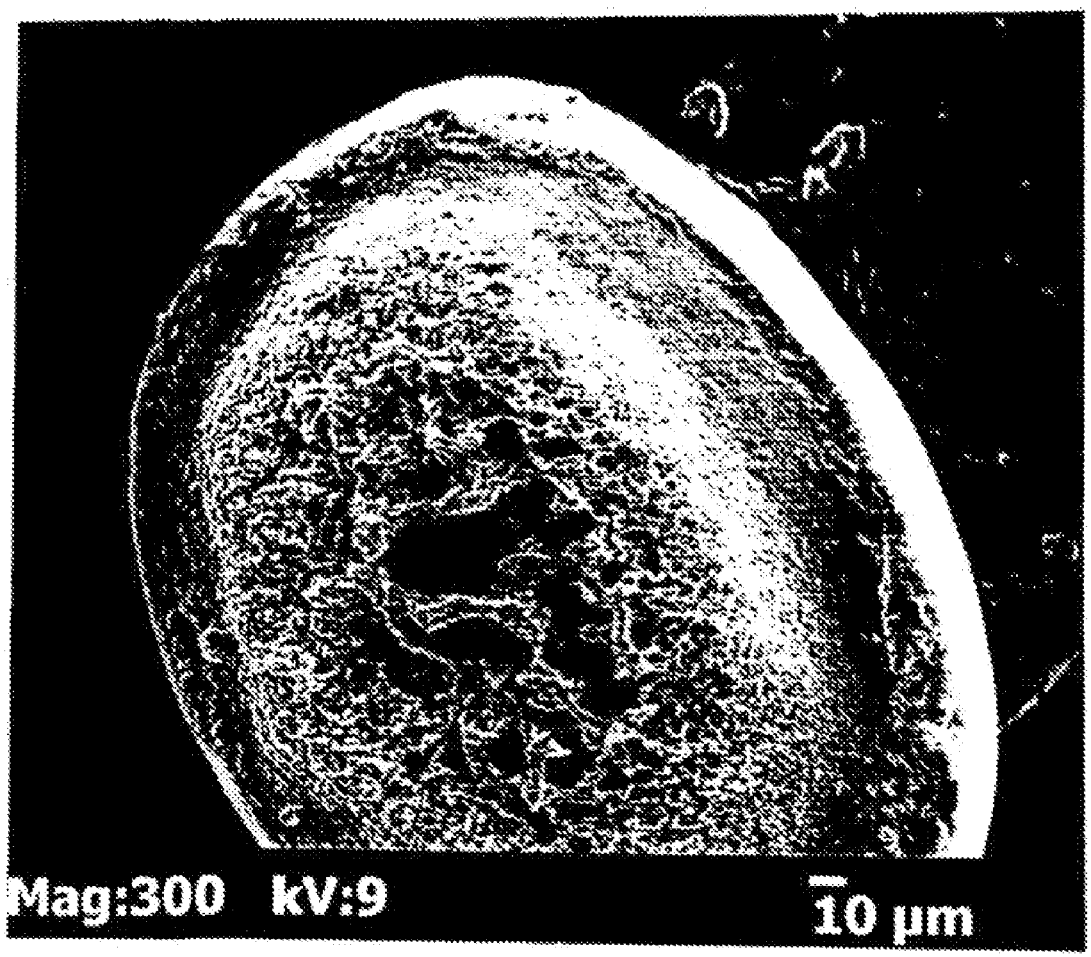

FIG. 2A shows an embodiment in which the embolic particles have a substantially uniform spherical shape and size. FIG. 2B shows an embodiment in which an embolic particle has a well-defined outer spherical surface including relatively small, randomly located pores. The surface appears substantially smooth, with a surface morphology including larger features, such as crevice-like features. FIGS. 2C-2E show scanning electron micrograph (SEM) images of cross-sections through embolic particles in which the bodies of the particles define pores which provide compressibility and other properties to the embolic composition. Pores near the center of the particle are relatively large, and pores near the surface of the particle are relatively small.

The region of small pores near the surface of the embolic particle is relatively stiff and incompressible, which enhances resistance to shear forces and abrasion. In addition, the variable pore size profile can produce a symmetric compressibility and, it is believed, a compressibility profile. As a result, the particles can be relatively easily compressed from a maximum, at rest diameter to a smaller, compressed first diameter, although compression to an even smaller diameter requires substantially greater force. Without wishing to be bound by theory, it is believed that a variable compressibility profile can be due to the presence of a relatively weak, collapsible inter-pore wall structure in the center region where the pores are large, and a stiffer inter-pore wall structure near the surface of the particle, where the pores are more numerous and relatively small. It is further believed that a variable pore size profile can enhance elastic recovery after compression. It is also believed that the pore structure can influence the density of the embolic particles and the rate of carrier fluid or body fluid uptake.

In some embodiments, the embolic particles can be delivered through a catheter having a lumen with a cross-sectional area that is smaller (e.g., about 50 percent or less) than the uncompressed cross-sectional area of the particles. In such embodiments, the embolic particles are compressed to pass through the catheter for delivery into the body. Typically, the compression force is provided indirectly, by depressing the syringe plunger to increase the pressure applied to the carrier fluid. In general, the embolic particles are relatively easily compressed to diameters sufficient for delivery through the catheter into the body. The relatively robust, rigid surface region can resist abrasion when the embolic particles contact hard surfaces such as syringe surfaces, hard plastic or metal stopcock surfaces, and the catheter lumen wall (made of, e.g., Teflon) during delivery. Once in the body, the embolic particles can substantially recover to original diameter and shape for efficient transport in the carrier and body fluid stream. At the point of occlusion, the particles can again compress as they aggregate in the occlusion region. The embolic particles can form a relatively dense occluding mass. The compression in the body is generally determined by the force provided by body fluid flow in the lumen. In some embodiments, the compression may be limited by the compression profile of the particles, and the number of embolic particles needed to occlude a given diameter may be reduced.

In some embodiments, among the particles delivered to a subject, the majority (e.g., about 50 percent or more, about 60 percent or more, about 70 percent or more, about 80 percent or more, about 90 percent or more) of the particles have a diameter of about 1500 microns or less (e.g., about 1200 microns or less, about 900 microns or less, about 700 microns or less, about 500 microns or less, about 300 microns or less) and/or about 10 microns or more (e.g., about 100 microns or more, about 300 microns or more, about 400 microns or more, about 500 microns or more, about 700 microns or more, about 900 microns or more).

In certain embodiments, the particles delivered to a subject have a mean diameter of about 1500 microns or less (e.g., about 1200 microns or less, about 900 microns or less, about 700 microns or less, about 500 microns or less, about 300 microns or less) and/or about 10 microns or more (e.g., about 100 microns or more, about 300 microns or more, about 400 microns or more, about 500 microns or more, about 700 microns or more, about 900 microns or more). Exemplary ranges for the mean diameter of particles delivered to a subject include from about 100 microns to about 300 microns, from about 300 microns to about 500 microns, from about 500 microns to about 700 microns, and from about 900 microns to about 1200 microns. In general, a collection of particles has a mean diameter in approximately the middle of the range of the diameters of the individual particles, and a variance of about 20 percent or less (e.g. about 15 percent or less, about 10 percent or less).

In some embodiments, the mean size of the particles delivered to a subject can vary depending upon the particular condition to be treated. As an example, in embodiments in which the particles are used to treat a liver tumor, the particles delivered to the subject can have a mean diameter of about 500 microns or less (e.g., from about 100 microns to about 300 microns, from about 300 microns to about 500 microns). As another example, in embodiments in which the particles are used to treat a uterine fibroid, the particles delivered to the subject can have a mean diameter of about 1200 microns or less (e.g., from about 500 microns to about 700 microns, from about 700 microns to about 900 microns, from about 900 microns to about 1200 microns).

As shown in FIG. 2C, in some embodiments a particle can be considered to include a center region, C, from the center c' of the particle to a radius of about r/3, a body region, B, from about r/3 to about 2 r/3 and a surface region, S, from 2r/3 to r. The regions can be characterized by the relative size of the pores in each region, the density of the pores (the number of pores per unit volume) in each region, and/or the material density (density of particle material per unit volume) in each region.

In general, the mean size of the pores in region C of a particle is greater than the mean size of the pores at region S of the particle. In some embodiments, the mean size of the pores in region C of a particle is greater than the mean size of the pores in region B the particle, and/or the mean size of the pores in region B of a particle is greater than the mean size of the pores at region S the particle. In some embodiments, the mean pore size in region C is about 20 microns or more (e.g., about 30 microns or more, from about 20 microns to about 35 microns). In certain embodiments, the mean pore size in region B is about 18 microns or less (e.g. about 15 microns or less, from about 18 microns to about two microns). In some embodiments, the mean pore size of the pores in region S is about one micron or less (e.g. from about 0.1 micron to about 0.01 micron). In certain embodiments, the mean pore size in region B is from about 50 percent to about 70 percent of the mean pore size in region C, and/or the mean pore size at region S is about 10 percent or less (e.g., about two percent or less) of the mean pore size in region B. In some embodiments, the surface of a particle and/or its region S is/are substantially free of pores having a diameter greater than about one micron (e.g., greater than about 10 microns). In certain embodiments, the mean pore size in the region from 0.8r to r (e.g., from 0.9r to r) is about one micron or less (e.g., about 0.5 micron or less, about 0.1 micron or less). In some embodiments, the region from the center of the particle to 0.9r (e.g., from the center of the particle to 0.8r) has pores of about 10 microns or greater and/or has a mean pore size of from about two microns to about 35 microns. In certain embodiments, the mean pore size in the region from 0.8r to r (e.g., from 0.9r to r) is about five percent or less (e.g., about one percent or less, about 0.3 percent or less) of the mean pore size in the region from the center to 0.9r. In some embodiments, the largest pores in the particles can have a size in the range of about one percent or more (e.g., about five percent or more, about 10 percent or more) of the particle diameter. The size of the pores in a particle can be measured by viewing a cross-section as in FIG. 2C. For irregularly shaped (nonspherical) pores, the maximum visible cross-section is used. In FIG. 2C, the SEM was taken on wet particles including absorbed saline, which were frozen in liquid nitrogen and sectioned. FIG. 2B was taken prior to sectioning. In FIGS. 2D-2E, the particle was freeze-dried prior to sectioning and SEM analysis.

Generally, the density of pores in region C of a particle is greater than the density of pores at region S of the particle. In some embodiments, the density of pores in region C of a particle is greater than the density of pores in region B of the particle, and/or the density of pores in region B of a particle is greater than the density of pores at region S of the particle.

In general, the material density in region C of a particle is less than the material density at region S of the particle. In some embodiments, the material density in region C of a particle is less than the material density in region B of the particle, and/or the material density in region B of a particle is less than the material density at region S of the particle.

In general, the density of a particle (e.g., as measured in grams of material per unit volume) is such that it can be readily suspended in a carrier fluid (e.g., a pharmaceutically acceptable carrier, such as a saline solution, a contrast solution, or a mixture thereof) and remain suspended during delivery. In some embodiments, the density of a particle is from about 1.1 grams per cubic centimeter to about 1.4 grams per cubic centimeter. As an example, for suspension in a saline-contrast solution, the density can be from about 1.2 grams per cubic centimeter to about 1.3 grams per cubic centimeter.

In certain embodiments, the sphericity of a particle after compression in a catheter (e.g., after compression to about 50 percent or more of the cross-sectional area of the particle) is about 0.9 or more (e.g., about 0.95 or more, about 0.97 or more). A particle can be, for example, manually compressed, essentially flattened, while wet to about 50 percent or less of its original diameter and then, upon exposure to fluid, regain a sphericity of about 0.9 or more (e.g., about 0.95 or more, about 0.97 or more).

Manufacture

Figure 3A:
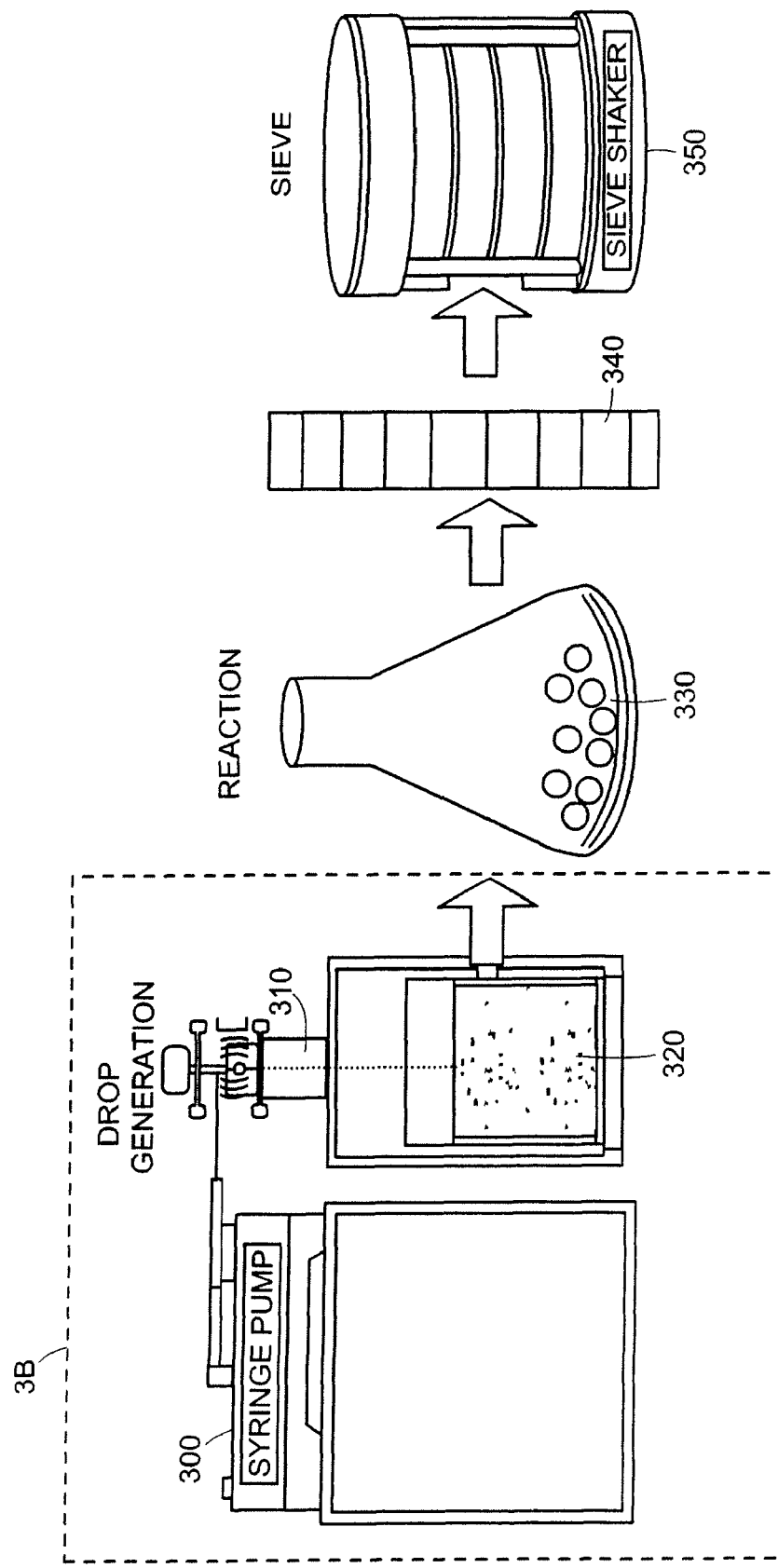
Figure 3B:
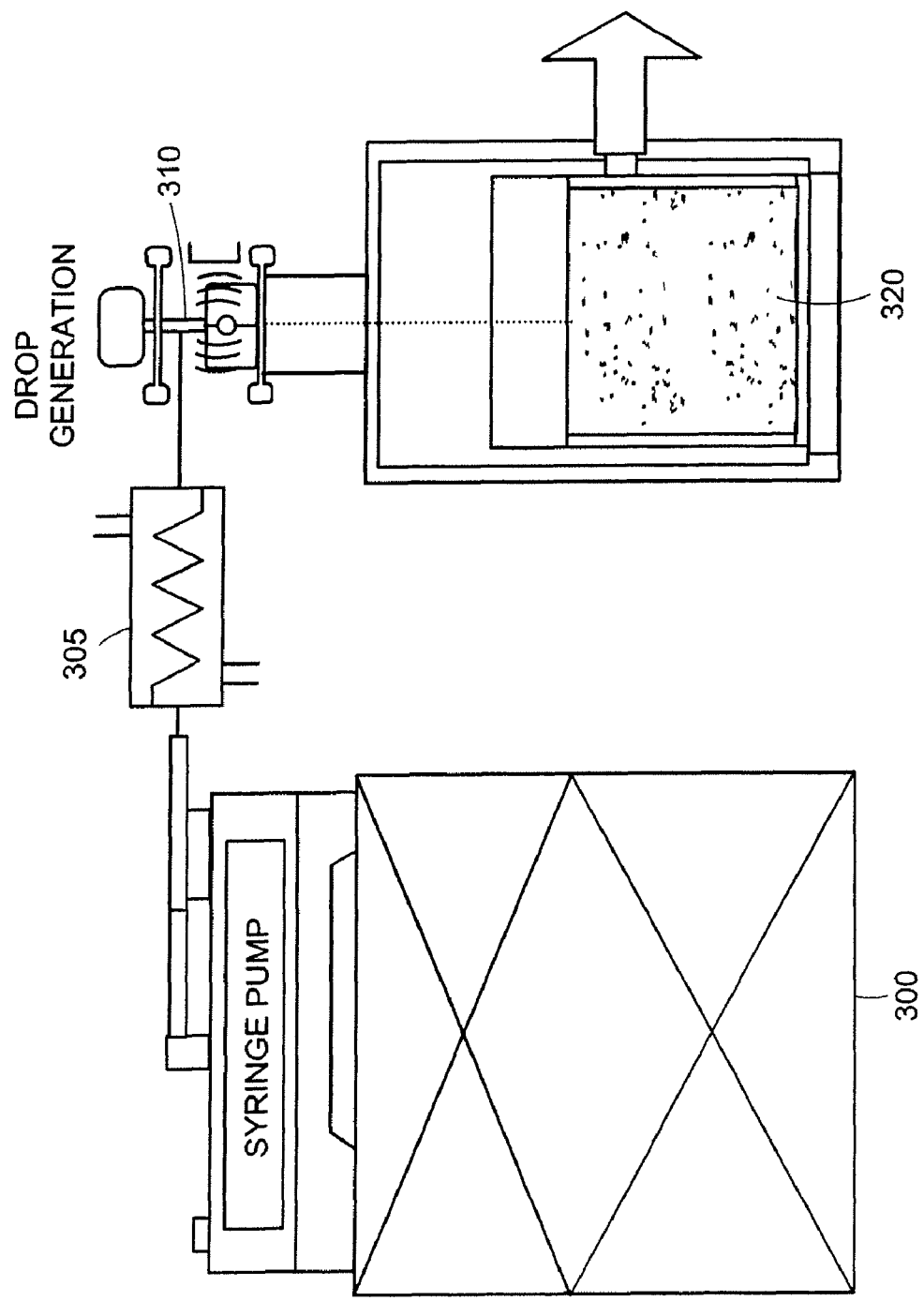
FIG. 3B is an enlarged schematic of region 3B in FIG. 3A.

FIG. 3A shows an embodiment of a system for producing embolic particles. The system includes a flow controller 300, a drop generator 310, a gelling vessel 320, a reactor vessel 330, a gel dissolution chamber 340 and a filter 350. As shown in FIG. 3B, flow controller 300 delivers polymer solutions to a viscosity controller 305, which heats the solution to reduce viscosity prior to delivery to drop generator 310. The solution passes through an orifice in a nozzle in drop generator 310, forming drops of the solution. The drops are then directed into gelling vessel 320, where the drops are stabilized by gel formation. The gel-stabilized drops are transferred from gelling vessel 320 to reactor vessel 330, where the polymer in the gel-stabilized drops is reacted, forming precursor particles. The precursor particles are transferred to gel dissolution chamber 340, where the gel is dissolved. The particles are then filtered in filter 350 to remove debris, and are sterilized and packaged as an embolic composition including embolic particles.

In general, a base polymer and a gelling precursor are dissolved in water and mixed.

Examples of base polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids (e.g., poly (d-lactic-co-glycolic) acids) and copolymers or mixtures thereof. A preferred polymer is polyvinyl alcohol (PVA). The polyvinyl alcohol, in particular, is typically hydrolyzed in the range of from about 80 percent to about 99 percent. The weight average molecular weight of the base polymer can be, for example, in the range of from about 9000 to about 186,000 (e.g., from about 85,000 to about 146,000, from about 89,000 to about 98,000).

Gelling precursors include, for example, alginates, alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyalauronic acid, locust beam gum, arabinogalactan, pectin, amylopectin, other water soluble polysaccharides and other ionically cross-linkable polymers. A particular gelling precursor is sodium alginate. A preferred sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which produces a high tensile, robust gel.

In some embodiments, the base polymer (e.g., PVA, such as high molecular weight PVA) can be dissolved in water by heating (e.g., above about 70° C. or more, about 121° C.), while the gelling precursor (e.g., an alginate) can be dissolved at room temperature. The base polymer (e.g., PVA) can be dissolved by mixing the base polymer and the gelling precursor (e.g., alginate) together in a vessel which is heated, e.g., to a temperature of at least about 50° C. (e.g., about 65° C. or more, about 75° C. or more, about 85° C. or more, about 95° C. or more, about 105° C. or more, about 115° C. or more, about 121° C.). In some embodiments, the mixture can be heated in an autoclave. Alternatively, the base polymer (e.g., PVA) can be disposed in water and heated. The gelling precursor (e.g., alginate) can subsequently be added at room temperature, to avoid exposing the alginate to high temperature. Heat can also be applied, for example, by microwave application.

In certain embodiments, such as when the base polymer is PVA and the gelling precursor is alginate, the mixture can be from about 6.5 weight percent to about 8.5 weight percent (e.g., about eight weight percent, about seven weight percent) base polymer and from about 1.5 weight percent to about 2.5 weight percent (e.g., about 1.75 weight percent, about two weight percent) gelling precursor.

In some embodiments, the base polymer/gelling precursor mixture can be introduced to a high pressure pumping apparatus, such as a syringe pump (e.g., model PHD4400, Harvard Apparatus, Holliston, Mass.), and then transferred to drop generator 310. Alternatively or additionally, drop generator 310 can contain a pressure control device that applies a pressure (e.g., from about 0.5 Bar to about 1.6 Bar) to the base polymer/gelling precursor mixture (a pressure head) to control the rate at which the mixture is transferred to drop generator 310.

The pressure can be selected, for example, based on the size of the nozzle orifice and/or the desired viscosity of the base polymer/gelling precursor mixture, and/or the desired size of the particles. In general, for a given mixture, as the nozzle orifice is decreased, the pressure is increased. Generally, for a given mixture, as the desired viscosity of the mixture is decreased, the temperature is increased. As an example, in embodiments in which the nozzle orifice has a diameter of about 100 microns and the base polymer/gelling precursor mixture has a viscosity of from about 60 centipoise to about 100 centipoise, the pressure can be about 1.55 Bar. As another example, in embodiments in which the nozzle orifice has a diameter of about 200 microns and the base polymer/gelling precursor mixture has a viscosity of from about 60 centipoise to about 100 centipoise, the pressure can be about 0.55 Bar.

Referring to FIG. 3B, viscosity controller 305 is a heat exchanger that circulates water at a predetermined temperature about the flow tubing between the pump and drop generator 310. The base polymer/gelling precursor mixture flows into viscosity controller 305, where the mixture is heated so that its viscosity is lowered to a desired level. Alternatively or additionally, the vessel containing the base polymer/gelling precursor mixture can be disposed in a heated fluid bath (e.g., a heated water bath) to heat the base polymer/gelling precursor mixture. In some embodiments (e.g., when the system does not contain viscosity controller 305), flow controller 300 and/or drop generator 310 can be placed in a temperature-controlled chamber (e.g. an oven, a heat tape wrap) to heat the base polymer/gelling precursor mixture.

The temperature to which the base polymer/gelling precursor mixture is heated prior to transfer to drop generator 310 can be selected, for example, based on the desired viscosity of the mixture and/or the size of the orifice in the nozzle. In general, for a given mixture, the lower the desired viscosity of the mixture, the higher the temperature to which the mixture is heated. Generally, for a given mixture, the smaller the diameter of the nozzle, the higher the temperature to which the mixture is heated. As an example, in embodiments in which nozzle has a diameter of from about 150 microns to about 300 microns and the desired viscosity of the mixture is from about 90 centipoise to about 200 centipoise, the mixture can be heated to a temperature of from about 60° C. to about 70° C. (e.g., about 65° C.). As another example, in embodiments in which the nozzle has a diameter of from about 100 microns to about 200 microns and the desired viscosity of the mixture is from about 60 centipoise to about 100 centipoise, the mixture can be heated to a temperature of from about 70° C. to about 80° C. (e.g., about 75° C.).

Drop generator 310 generates substantially spherical drops of a predetermined diameter by forcing a stream of the base polymer/gelling precursor mixture through the nozzle orifice. The nozzle is subjected to a periodic disturbance to break up the jet stream of the mixture into drops of the mixture. The jet stream can be broken into drops by vibratory action generated, for example, by an electrostatic or piezoelectric element. The drop size can be controlled, for example, by controlling the nozzle orifice diameter, base polymer/gelling precursor flow rate, nozzle vibration amplitude, and nozzle vibration frequency. In general, holding other parameters constant, increasing the nozzle orifice diameter results in formation of larger drops, and increasing the flow rate results in larger drops. Generally, holding other parameters constant, increasing the nozzle vibration amplitude results in larger drops, and reducing the nozzle vibration frequency results in larger drops. In general, the nozzle orifice diameter can be about 500 microns or less (e.g., about 400 microns or less, about 300 microns or less, about 200 microns or less, about 100 microns or less) and/or about 50 microns or more. The flow rate through the drop generator is typically from about one milliliter per minute to about 12 milliliters per minute. Generally, the nozzle frequency used can be about 0.1 KHz or more (e.g., about 0.8 KHz or more, about 1.5 KHz or more, about 1.75 KHz or more, about 1.85 KHz or more, about 2.5 KHz or more, from about 0.1 KHz to about 0.8 KHz). In general, the nozzle vibration amplitude is larger than the width of the jet stream. The drop generator can have a variable nozzle vibration amplitude setting, such that an operator can adjust the amplitude of the nozzle vibration. In some embodiments, the nozzle vibration amplitude is set at between about 80 percent and about 100 percent of the maximum setting.

In some embodiments, drop generator 310 can charge the drops after formation, such that mutual repulsion between drops prevents drop aggregation as the drops travel from drop generator 310 to gelling vessel 320. Charging may be achieved, for example, by an electrostatic charging device such as a charged ring positioned downstream of the nozzle.

An example of a commercially available electrostatic drop generator is the model NISCO Encapsulation unit VAR D (NISCO Engineering, Zurich, Switzerland). Another example of a commercially available drop generator is the Inotech Encapsulator unit IE-50R/NS (Inotech AG, Dottikon, Switzerland).

Drops of the base polymer and gelling precursor mixture are captured in gelling vessel 320. The distance between gelling vessel 320 and the orifice of the nozzle in drop generator 310 is generally selected so that the jet stream of the base polymer/gelling precursor mixture is substantially broken up into discrete drops before reaching gelling vessel 320. In some embodiments, the distance from the nozzle orifice to the mixture contained in gelling vessel 320 is from about five inches to about six inches.

The mixture contained in gelling vessel 320 includes a gelling agent which interacts with the gelling precursor to stabilize drops by forming a stable gel. Suitable gelling agents include, for example, a divalent cation such as alkali metal salt, alkaline earth metal salt or a transition metal salt that can ionically cross-link with the gelling agent. An inorganic salt, for example, a calcium, barium, zinc or magnesium salt can be used as a gelling agent. In embodiments, particularly those using an alginate gelling precursor, a suitable gelling agent is calcium chloride. The calcium cations have an affinity for carboxylic groups in the gelling precursor. The cations complex with carboxylic groups in the gelling precursor, resulting in encapsulation of the base polymer in a matrix of gelling precursor.

Without wishing to be bound by theory, it is believed that in some embodiments (e.g., when forming particles having a diameter of about 500 microns or less), it can be desirable to reduce the surface tension of the mixture contained in gelling vessel 320. This can be achieved, for example, by heating the mixture in gelling vessel 320 (e.g., to a temperature greater than room temperature, such as a temperature of about 30° C. or more), by bubbling a gas (e.g., air, nitrogen, argon, krypton, helium, neon) through the mixture contained in gelling vessel 320, by stirring (e.g., via a magnetic stirrer) the mixture contained in gelling vessel 320, by including a surfactant in the mixture containing the gelling agent, and/or by forming a mist containing the gelling agent above the mixture contained in gelling vessel 320 (e.g., to reduce the formation of tails and/or enhance the sphericity of the particles).

Figure 4:
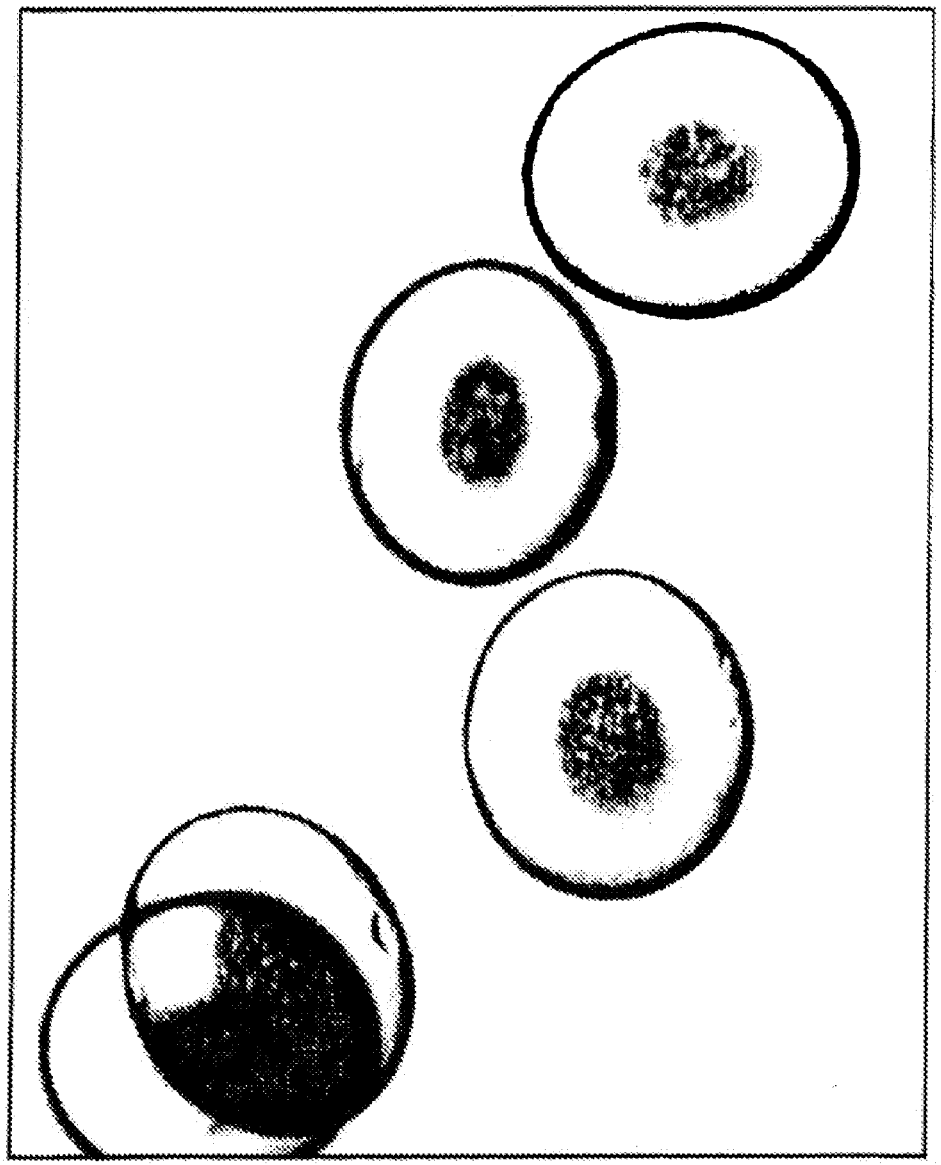
FIG. 4 is a photograph of gel-stabilized drops.

FIG. 4 shows a photo-image of the gelled particles. As evident, a pore structure in the particle forms in the gelling stage. The concentration of the gelling agent can affect pore formation in the particle, thereby controlling the porosity gradient in the particle. Adding non-gelling ions (e.g., sodium ions) to the gelling solution can reduce the porosity gradient, resulting in a more uniform intermediate porosity throughout the particle. In embodiments, the gelling agent is, for example, from about 0.01 weight percent to about 10 weight percent (e.g., from about one weight percent to about five weight percent, about two weight percent) in deionized water. In embodiments, particles, including gelling agent and a pore structure, can be used in embolic compositions.

Following drop stabilization, the gelling solution can be decanted from the solid drops, or the solid drops can be removed from the gelling solution by sieving. The solid drops are then transferred to reactor vessel 330, where the base polymer in the solid drops is reacted (e.g., cross-linked) to produce precursor particles.

Reactor vessel 330 contains an agent that chemically reacts with the base polymer to cause cross-linking between polymer chains and/or within a polymer chain. The agent diffuses into the solid drops from the surface of the particle in a gradient which, it is believed, provides more cross-linking near the surface of the solid drop than in the body and center of the drop. Reaction is greatest at the surface of a solid drop, providing a stiff, abrasion-resistant exterior. For polyvinyl alcohol, for example, vessel 330 includes one or more aldehydes, such as formaldehyde, glyoxal, benzaldehyde, aterephthalaldehyde, succinaldehyde and glutaraldehyde for the acetalization of polyvinyl alcohol. Vessel 330 also includes an acid, for example, strong acids such as sulfuric acid, hydrochloric acid, nitric acid and weak acids such as acetic acid, formic acid and phosphoric acid. In embodiments, the reaction is primarily a 1,3-acetalization:

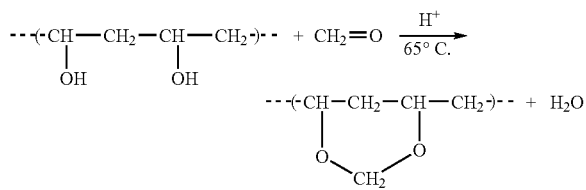

This intra-chain acetalization reaction can be carried out with relatively low probability of inter-chain cross-linking, as described in John G. Pritchard, "Poly(Vinyl Alcohol) Basic Properties and Uses (Polymer Monograph, vol. 4) (see p. 93-97), Gordon and Breach, Science Publishers Ltd., London, 1970, which is incorporated herein by reference. Because the reaction proceeds in a random fashion, some OH groups along a polymer chain might not react with adjacent groups and may remain unconverted.

Adjusting for the amounts of aldehyde and acid used, reaction time and reaction temperature can control the degree of acetalization. In embodiments, the reaction time is from about five minutes to about one hour (e.g., from about 10 minutes to about 40 minutes, about 20 minutes). The reaction temperature can be, for example, from about 25° C. to about 150° C. (e.g., from about 75° C. to about 130° C., about 65° C.). Reactor vessel 330 can be placed in a water bath fitted with an orbital motion mixer. The cross-linked precursor particles are washed several times with deionized water to neutralize the particles and remove any residual acidic solution.

The precursor particles are transferred to dissolution chamber 340, where the gelling precursor is removed (e.g., by an ion exchange reaction). In embodiments, sodium alginate is removed by ion exchange with a solution of sodium hexa-metaphosphate (EM Science). The solution can include, for example, ethylenediaminetetracetic acid (EDTA), citric acid, other acids, and phosphates. The concentration of the sodium hexa-metaphosphate can be, for example, from about one weight percent to about 20 weight percent (e.g., from about one weight percent to about ten weight percent, about five weight percent) in deionized water. Residual gelling precursor (e.g., sodium alginate) can be measured by assay (e.g., for the detection of uronic acids in, for example, alginates containing mannuronic and guluronic acid residues). A suitable assay includes rinsing the particles with sodium tetraborate in sulfuric acid solution to extract alginate, combining the extract with metahydroxydiphenyl colormetric reagent, and determining concentration by UV/VIS spectroscopy. Testing can be carried out by alginate suppliers such as FMC Biopolymer, Oslo, Norway. Residual alginate may be present in the range of, for example, from about 20 weight percent to about 35 weight percent prior to rinsing, and in the range of from about 0.01 weight percent to about 0.5 weight percent (e.g., from about 0.1 weight percent to about 0.3 weight percent, about 0.18 weight percent) in the particles after rinsing for 30 minutes in water at about 23° C.

The particles are filtered through filter 350 to remove residual debris. Particles of from about 100 microns to about 300 microns can filtered through a sieve of about 710 microns and then a sieve of about 300 microns. The particles can then be collected on a sieve of about 20 microns. Particles of from about 300 to about 500 microns can filtered through a sieve of about 710 microns and then a sieve of about 500 microns. The particles can then be collected on a sieve of about 100 microns. Particles of from about 500 to about 700 microns can be filtered through a sieve of about 1000 microns, then filtered through a sieve of about 710 microns, and then a sieve of about 300 microns. The particles can then be collected in a catch pan. Particles of from about 700 to about 900 microns can be filtered through a sieve of 1000 microns and then a sieve of 500 microns. The particles can then be collected in a catch pan. Particles of from about 900 to about 1200 microns can filtered through a sieve of 1180 microns and then a sieve of 710 microns. The particles can then be collected in a catch pan.

The particles are then packaged. Typically, from about one milliliter to about five milliliters of particles are packaged in from about five milliliters to about ten milliliters of saline. The filtered particles then are typically sterilized by a low temperature technique, such as e-beam irradiation. In embodiments, electron beam irradiation can be used to pharmaceutically sterilize the particles (e.g., to reduce bioburden). In e-beam sterilization, an electron beam is accelerated using magnetic and electric fields, and focused into a beam of energy. The resultant energy beam can be scanned by means of an electromagnet to produce a "curtain" of accelerated electrons. The accelerated electron beam penetrates the collection of particles, destroying bacteria and mold to sterilize and reduce the bioburden in the particles. Electron beam sterilization can be carried out by sterilization vendors such as Titan Scan, Lima, Ohio.

The embolic compositions can be used in the treatment of, for example, fibroids, tumors, internal bleeding, AVMs, hypervascular tumors, fillers for aneurysm sacs, endoleak sealants, arterial sealants, puncture sealants and occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

The magnitude of a dose of an embolic composition can vary based on the nature, location and severity of the condition to be treated, as well as the route of administration. A physician treating the condition, disease or disorder can determine an effective amount of embolic composition. An effective amount of embolic composition refers to the amount sufficient to result in amelioration of symptoms or a prolongation of survival of the patient. The embolic compositions can be administered as pharmaceutically acceptable compositions to a patient in any therapeutically acceptable dosage, including those administered to a patient intravenously, subcutaneously, percutaneously, intratrachealy, intramuscularly, intramucosaly, intracutaneously, intra-articularly, orally or parenterally.

In some embodiments, a composition containing the particles can be used to prophylactically treat a condition.

Compositions containing the particles can be prepared in calibrated concentrations of the particles for ease of delivery by the physician. Suspensions of the particles in saline solution can be prepared to remain stable (e.g., to not precipitate) over a duration of time. A suspension of the particles can be stable, for example, for from about one minute to about 20 minutes (e.g. from about one minute to about ten minutes, from about two minutes to about seven minutes, from about three minutes to about six minutes). The concentration of particles can be determined by adjusting the weight ratio of the particles to the physiological solution. If the weight ratio of the particles is too small, then too much liquid could be injected into a blood vessel, possibly allowing the particles to stray into lateral vessels. In some embodiments, the physiological solution can contain from about 0.01 weight percent to about 15 weight percent of the particles. A composition can include a mixture of particles, such as particles having the pore profiles discussed above, particles with other pore profiles, and/or non-porous particles.

While certain embodiments have been described, the invention is not so limited.

As an example, particles can be used for embolic applications without removal of the gelling agent (e.g. alginate). Such particles can be prepared, for example, as described above, but without removing the alginate from the particle after cross-linking.

As another example, while substantially spherical particles are preferred, non-spherical particles can be manufactured and formed by controlling, for example, drop formation conditions. In some embodiments, nonspherical particles can be formed by post-processing the particles (e.g., by cutting or dicing into other shapes).

Moreover, in some embodiments the particles can include one or more therapeutic agents (e.g., drugs). The therapeutic agent(s) can be in and/or on the particles. Therapeutic agents include agents that are negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); cells (of human origin, from an animal source, or genetically engineered); stem cells; immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); anti-inflammatory agents; calcium entry blockers; antineoplastic/antiproliferative/anti-mitotic agents (e.g., paclitaxel, doxorubicin, cisplatin); antimicrobials; anesthetic agents; anticoagulants; vascular cell growth promoters; vascular cell growth inhibitors; cholesterol-lowering agents; vasodilating agents; agents which interfere with endogenous vasoactive mechanisms; and survival genes which protect against cell death. Therapeutic agents are described in co-pending U.S. patent application Ser. No. 10/615,276, filed on Jul. 8, 2003, and entitled "Agent Delivery Particle", which is incorporated herein by reference.

In addition, in some embodiments (e.g., where the base polymer is a polyvinyl alcohol and the gelling precursor is alginate), after contacting the particles with the gelling agent but before cross-linking, the particles can be physically deformed into a specific shape and/or size. For example, the particles can be molded, compressed, punched, and/or agglomerated with other particles. After shaping, the base polymer (e.g., polyvinyl alcohol) can be cross-linked, optionally followed by substantial removal of the gelling precursor (e.g., alginate). Particle shaping is described, for example, in co-pending U.S. patent application Ser. No. 10/402,068, filed Mar. 28, 2003, and entitled "Forming a Chemically Cross-Linked Particle of a Desired Shape and Diameter", which is incorporated herein by reference.

Furthermore, in some embodiments the particles can be used for tissue bulking. As an example, the particles can be placed (e.g., injected) into tissue adjacent a body passageway. The particles can narrow the passageway, thereby providing bulk and allowing the tissue to constrict the passageway more easily. The particles can be placed in the tissue according to a number of different methods, for example, percutaneously, laparoscopically, and/or through a catheter. In certain embodiments, a cavity can be formed in the tissue, and the particles can be placed in the cavity. Particle tissue bulking can be used to treat, for example, intrinsic sphincteric deficiency (ISD), vesicoureteral reflux, gastroesophageal reflux disease (GERD), and/or vocal cord paralysis (e.g., to restore glottic competence in cases of paralytic dysphonia). In some embodiments, particle tissue bulking can be used to treat urinary incontinence and/or fecal incontinence. The particles can be used as a graft material or a filler to fill and/or to smooth out soft tissue defects, such as for reconstructive or cosmetic applications (e.g., surgery). Examples of soft tissue defect applications include cleft lips, scars (e.g., depressed scars from chicken pox or acne scars), indentations resulting from liposuction, wrinkles (e.g., glabella frown wrinkles), and soft tissue augmentation of thin lips. Tissue bulking is described, for example, in co-pending U.S. patent application Ser. No. 10/231,664, filed on Aug. 30, 2002, and entitled "Tissue Treatment", which is incorporated herein by reference.

The following examples are intended as illustrative and nonlimiting.

EXAMPLE 1

Particles were prepared as follows.

An aqueous solution containing eight weight percent polyvinyl alcohol (99+ percent hydrolyzed, average $M_w$ 89,000-120,000 (Aldrich)) and two weight percent sodium alginate (PRONOVA UPLVG, (FMC BioPolymer, Princeton, N.J.)) in deionized water was prepared. The solution was heated to about 121° C. The solution had a viscosity of about 310 centipoise at room temperature and a viscosity of about 160 centipoise at 65° C. Using a model PHD4400 syringe pump (Harvard Apparatus, Holliston, Mass.), the mixture was fed into a model NISCO Encapsulation unit VAR D drop generator (NISCO Engineering, Zurich, Switzerland). Drops generated by the drop generator were directed into a gelling vessel containing two weight percent calcium chloride in deionized water, and stirred with a stirring bar. The calcium chloride solution was decanted within about three minutes to avoid substantial leaching of the polyvinyl alcohol from the drops into the solution. The drops were added to a reaction vessel containing a solution of four weight percent formaldehyde (37 weight percent in methanol) and 20 weight percent sulfuric acid (95-98 percent concentrated). The reaction solution was stirred at 65° C. for 20 minutes. Precursor particles were rinsed with deionized water (3×300 milliliters) to remove residual acidic solution. The sodium alginate was substantially removed by soaking the precursor particles in a solution of five weight percent sodium hexa-methaphosphate in deionized water for 0.5 hour. The solution was rinsed in deionized water to remove residual phosphate and alginate. The particles were filtered by sieving, as discussed above, placed in saline (USP 0.9 percent NaCl) and sterilized by irradiation sterilization.

Particles were produced at the nozzle diameters, nozzle frequencies and flow rates (amplitude about 80 percent of maximum) described in Table I.

TABLE I

| Particle Size (microns) | Nozzle Diameter (microns) | Frequency (kHz) | Flow Rate (mL/min) | Density (g/mL) | Sphericity | Suspendability (minutes) |
|---|---|---|---|---|---|---|
| 500-700 | 150 | 0.45 | 4 | — | 0.92 | 3 |
| 700-900 | 200 | 0.21 | 5 | 1.265 | 0.94 | 5 |
| 900-1200 | 300 | 0.22 | 10 | — | 0.95 | 6 |

Suspendability was measured at room temperature by mixing a solution of two milliliters of particles in five milliliters of saline with contrast solution (Omnipaque 300, Nycomed, Buckinghamshire, UK), and observing the time for about 50 percent of the particles to enter suspension (i.e., not to have sunk to the bottom or floated to the top of a container having a volume of about ten milliliters and a diameter of about 25 millimeters). Suspendability provides a practical measure of how long the particles will remain suspended in use.

Measurements were also made of the amount of time that the particles remained suspended in the contrast solution. The particles remained in suspension for from about two to about three minutes.

Omnipaque 300 is an aqueous solution of Iohexol, N.N.-Bis (2,3-dihydroxypropyl)-T-[N-(2,3-dihydroxypropyl)-acetamide]-2,4,6-trilodo-isophthalmide. Omnipaque 300 contains 647 milligrams of iohexol equivalent to 300 milligrams of organic iodine per milliliter. The specific gravity of Omnipaque 300 is 1.349 of 37° C., and Omnipaque 300 has an absolute viscosity 11.8 centipoise at 20° C.

Particle size uniformity and sphericity were measured using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The system software identifies and measures particles in an image in the form of a fiber, rod or sphere. Sphericity computation and other statistical definitions are in Appendix A, attached, which is a page from the RapidVUE operating manual.

Figure 5:
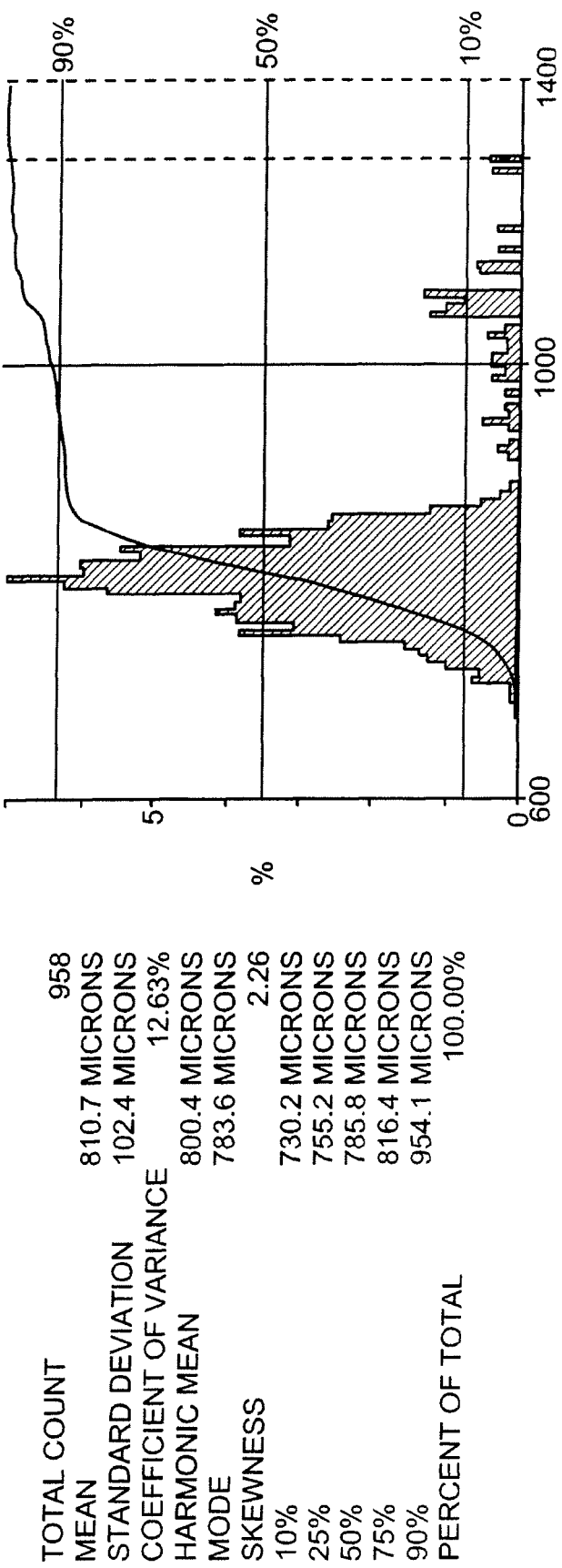
FIG. 5 is a graph of embolic particle size uniformity.

Referring to FIG. 5, particle size uniformity is illustrated for particles having a diameter of from about 700 microns to about 900 microns. The x-axis is the particle diameter, and the y-axis is the volume-normalized percentage of particles at each particle size. The total volume of particles detected was computed, and the volume of the particles at each diameter was divided by the total volume. The embolic particles had a distribution of particle sizes with variance of less than about ±15 percent.

EXAMPLE 2

Particles were prepared as follows.

An aqueous solution containing 7.06 weight percent polyvinyl alcohol (99+ percent hydrolyzed, average $M_w$ 89,000-120,000 (Aldrich)) and 1.76 weight percent sodium alginate (PRONOVA UPLVG, (FMC BioPolymer, Princeton, N.J.)) was prepared. The solution was heated to about 121° C. The solution had a viscosity of about 140 centipoise at room temperature, and a viscosity of about 70 centipoise at 65° C. Using a pressurized vessel, the mixture was fed to a drop generator (Inotech Encapsulator unit IE-50R/NS, Inotech Biosystems International, Inc.). Drops generated by the drop generator were directed into a gelling vessel containing two weight percent calcium chloride in deionized water, and stirred with a stirring bar. The drops were collected within about three minutes to avoid substantial leaching of the polyvinyl alcohol from the drops into the solution. The drops were added to a reaction vessel containing a solution of four weight percent formaldehyde (37 weight percent in methanol) and 20 weight percent sulfuric acid (95-98 percent concentrated). The reaction solution was stirred at 65° C. for 20 minutes. The precursor particles were rinsed with deionized water (3×300 milliliters) to remove residual acidic solution. The sodium alginate was substantially removed by soaking the precursor particles in a solution of five weight percent sodium hexa-methaphosphate in deionized water for half an hour. The solution was rinsed in deionized water to remove residual phosphate and alginate. The particles were filtered by sieving, placed in saline (USP 0.9 percent NaCl) and sterilized by irradiation sterilization.

The particles were produced at the nozzle diameters, nozzle frequencies and pressures (amplitude about 80 percent of maximum) described in Table II.

TABLE II

| Particle Size (microns) | Nozzle Diameter (microns) | Frequency (KHz) | Pressure (Bar) | Flow Rate (mL/min) | Suspendability (minutes) |
|---|---|---|---|---|---|
| 100-300 | 100 | 2.5 | 1.55 | 2.5 | 0.25 |
| 300-500 | 200 | 1.85 | 0.55 | 6.8 | 1 |

Suspendability was measured as described in Example 1.

Measurements were also made of the amount of time that the particles remained suspended in the contrast solution. The particles remained suspended in the contrast solution for about 20 minutes.

Figure 6:
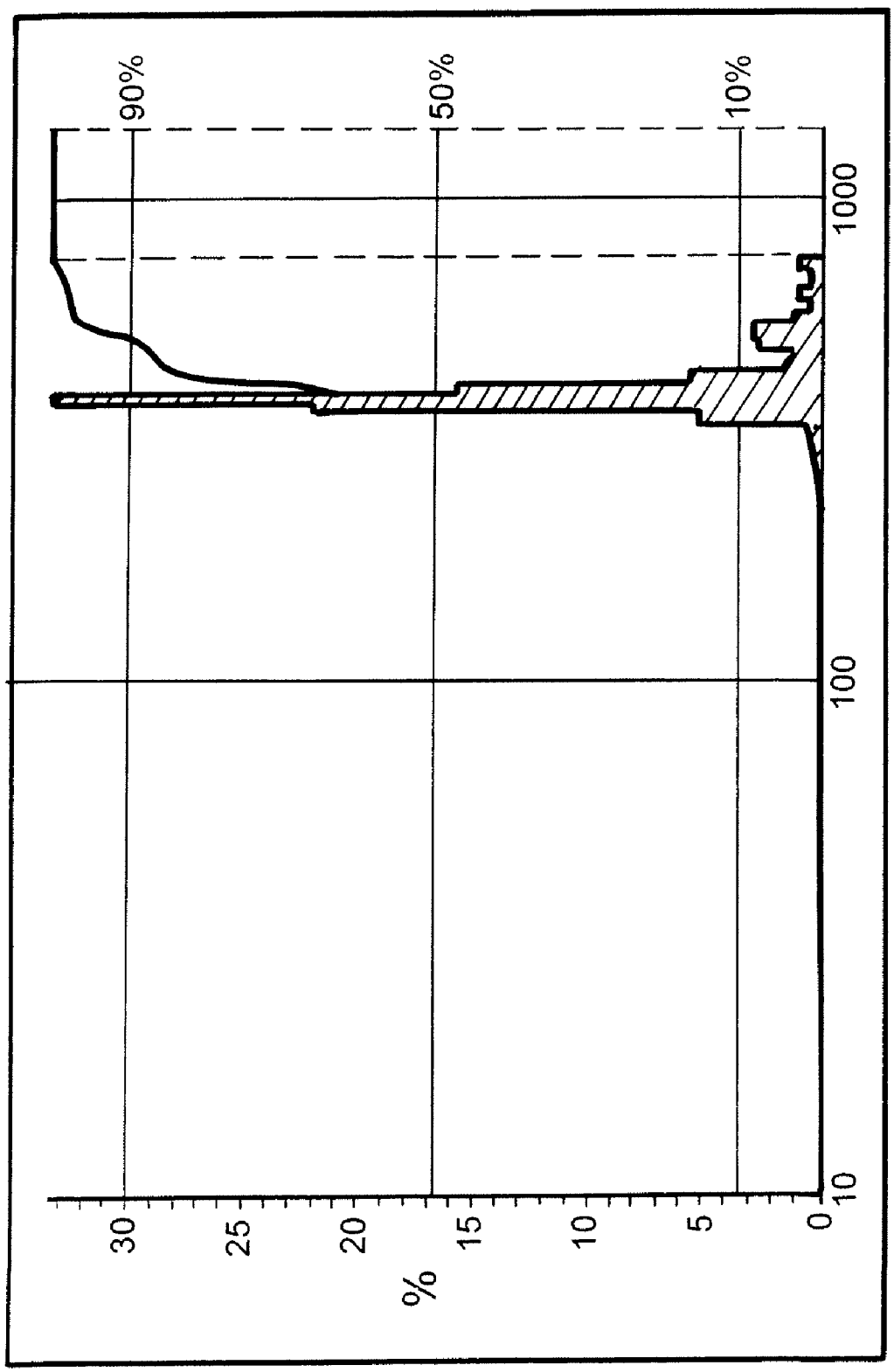
FIG. 6 is a graph of embolic particle size uniformity.

FIG. 6 shows particle size uniformity for particles having a diameter of from about 300 microns to about 500 microns (see discussion in Example 1). The embolic particles had a distribution of particle sizes with a variance of less than about ±15 percent.

EXAMPLE 3

Figure 7:
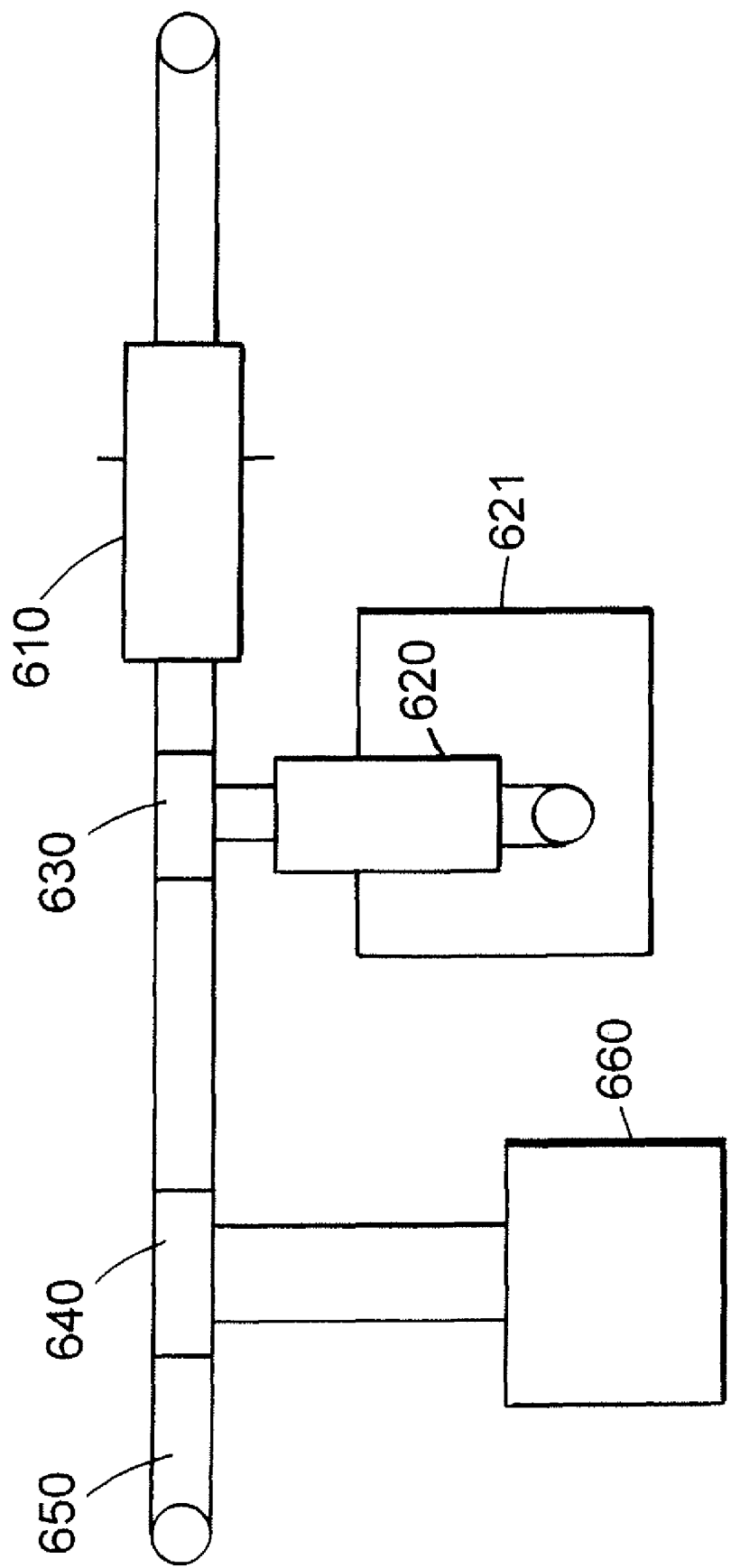
FIG. 7 is a schematic of an injection pressure testing equipment.

Referring to FIG. 7, a catheter compression test was used to investigate the injectability, and indirectly, the compressibility, of the particles. The test apparatus included a reservoir syringe 610 and an injection syringe 620 coupled to a T-valve 630. Reservoir syringe 610 was a 20 milliliter syringe while injection syringe 620 was a three milliliter syringe. T-valve 630 was coupled in series to a second T-valve 640. T-valve 640 was coupled to a catheter 650 and a pressure transducer 660. Injection syringe 620 was coupled to a syringe pump 621 (Harvard Apparatus).

To test deliverability of the particles, syringes 610 and 620 were loaded with embolic composition in saline and contrast agent (50/50 Ominipaque 300). The embolic composition in syringes 610 and 620 was intermixed by turning the T-valve to allow fluid between the syringes to mix and suspend the particles. After mixing, the embolic composition in syringe 620 flowed at a rate of about ten milliliters per minute. The back pressure generated in catheter 650 was measured by the pressure transducer 660 in millivolts to measure the clogging of catheter 650. About one milliliter of the particles was mixed in ten milliliters of solution.

Results for several different catheters (available from Boston Scientific, Natick, Mass.) and particle sizes are shown in Table III. The baseline pressure was the pressure observed when injecting carrier fluid only. The delivery pressure was the pressure observed while delivering particles in carrier fluid. The average was the average of the peak pressure observed in the three runs.

As evident, particles in each of the size ranges were successfully delivered without clogging catheters with a lumen diameter smaller than the largest particle size. The particles exhibited a post-compression sphericity of about 0.9 or more.

EXAMPLE 4

Solubility was tested by mixing particles in a solution of solvent at room temperature for about 0.5 hour and observing the mixture for visible signs of dissolution. The particles were insoluble in DMSO (dimethylsulfoxide), HFIP (hexafluoroisopropanol), and THF (tetrahydrofuran).

EXAMPLE 5

Particles had the following glass transition temperatures, as measured by differential scanning calorimetry data (DSC):

| Size (microns) | Glass Transition Temperature (° C.) |
|---|---|
| 100-300 | 107-108 |
| 300-500 | 110-111 |
| 500-700 | 109.30-110.14 |
| 900-1200 | 108.30-111.87 |

EXAMPLE 6

Figure 8:
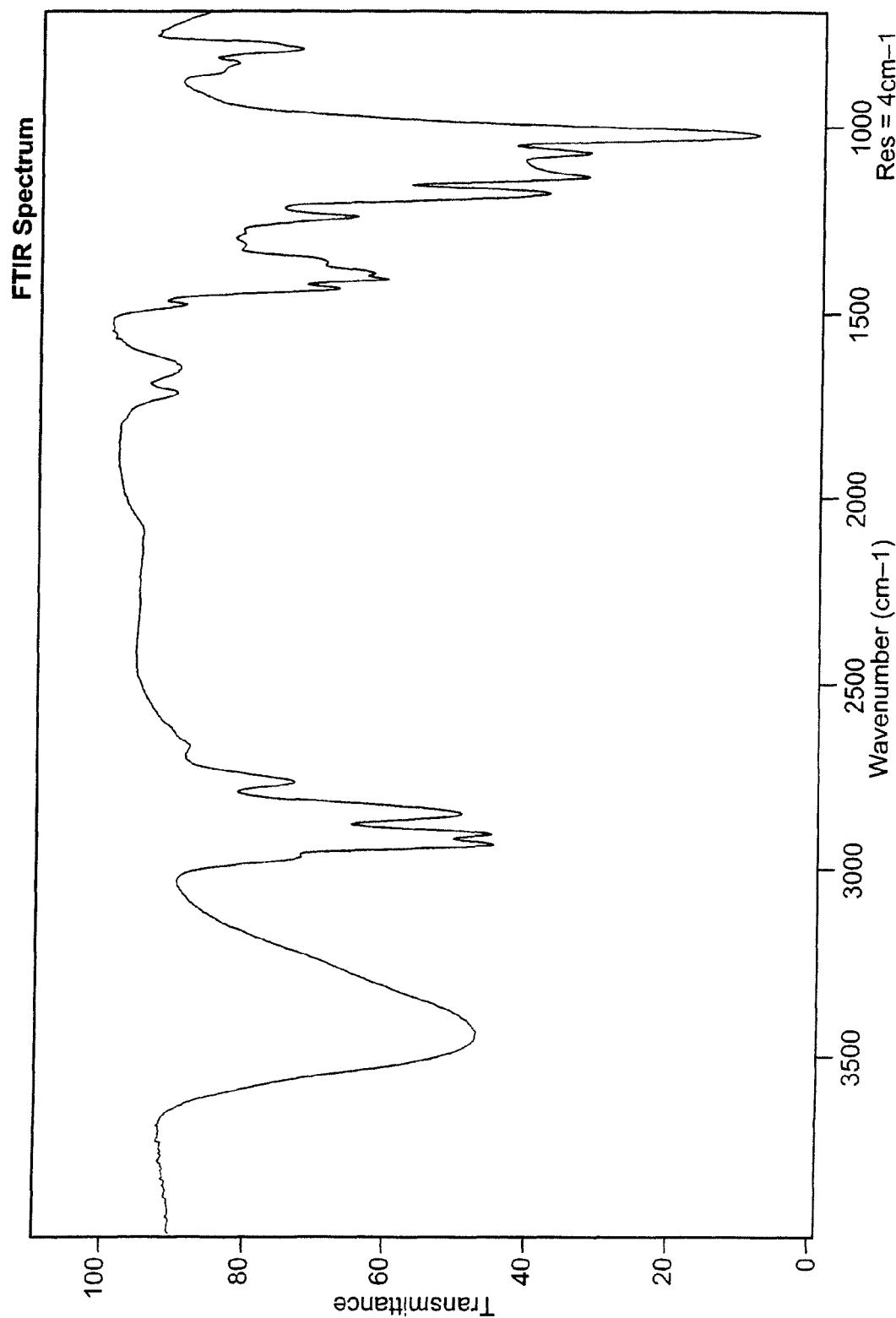
FIG. 8 is an infrared spectrum of embolic particles.
Figure 9:
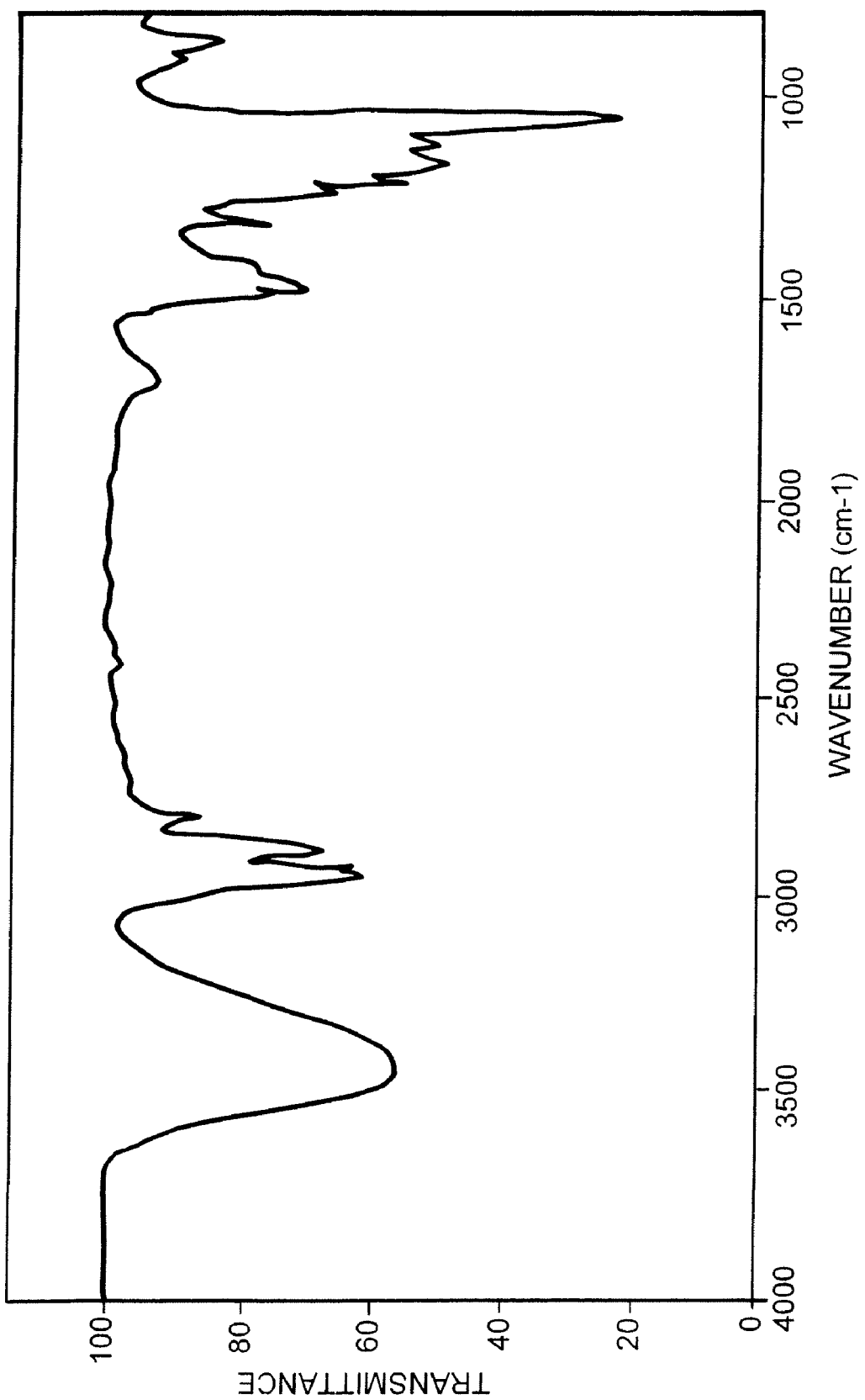
FIG. 9 is an infrared spectrum of embolic particles.

FIGS. 8 and 9 show the ATR infrared spectra of dried particles prepared according to Examples 1 and 2, respectively.

Other embodiments are in the claims.

What is claimed is:

1. A composition, comprising:
 a plurality of particles, at least some of the plurality of particles comprising cross-linked polyvinyl alcohol and having a diameter of about 500 microns or less, the at least some of the particles having a first average pore size in an interior region and a second average pore size at a surface region, the first average pore size being greater than the second average pore size; and
 a carrier fluid, the plurality of particles being in the carrier fluid.

2. The composition of claim 1, wherein the at least some of the particles have an average diameter of about 10 microns or more.

3. The composition of claim 1, wherein the at least some of the particles have an average diameter of about 100 microns or more.

4. The composition of claim 1, wherein the at least some of the particles have an average diameter of about 300 microns or less.

TABLE III

| SIZE (microns) | Delivery Catheter | Inner Diameter (microns) | Avg. Baseline Pressure (psia) | Avg. Delivery Pressure (psia) | Total number of Clogs |
|---|---|---|---|---|---|
| 100-300 | Spinnaker Elite ® | 279 | 71.3 | 65.4 | 0 |
| 300-500 | Spinnaker Elite ® | 330 | 54.6 | 52.6 | 0 |
| 500-700 | RENEGADE ® | 533 | 32.610 | 33.245 | 0 |
| 700-900 | FASTRACKER ® | 609 | 11.869 | 13.735 | 0 |
| 900-1200 | GLIDECATH ® | 965 | 0.788 | 0.864 | 0 |

5. The composition of claim 1, wherein the at least some of the particles have an average diameter of about 300 microns or more.

6. The composition of claim 1, wherein the at least some of the particles are at least partially coated with a substantially bioabsorbable material.

7. The composition of claim 1, wherein the at least some of the particles have a density of from about 1.1 grams per cubic centimeter to about 1.4 grams per cubic centimeter.

8. The composition of claim 1, wherein the at least some of the particles have an average sphericity of about 0.9 or more.

9. The composition of claim 1, wherein, after compression to about 50 percent, the at least some of the particles have an average sphericity of about 0.9 or more.

10. The composition of claim 1, wherein the at least some of the particles comprise about 2.5 weight percent or less polysaccharide.

11. The composition of claim 10, wherein the polysaccharide comprises alginate.

12. The composition of claim 11, wherein the alginate has a guluronic acid content of about 60 percent or greater.

13. The composition of claim 1, wherein the at least some of the particles are substantially insoluble in DMSO.

14. The composition of claim 1, wherein the at least some of the particles are substantially free of animal-derived compounds.

15. The composition of claim 1, wherein the at least some of the particles have a first density of pores in the interior region and a second density of pores at a surface region, and the first density is different from the second density.

16. A composition, comprising:
    a plurality of particles, at least some of the plurality of particles comprising polysaccharide and having a diameter of about 500 microns or less, the at least some of the particles having an interior region defining pores and a surface region defining pores, the at least some of the particles having a first density of pores in the interior region and a second density of pores at the surface region, the first density being different from the second density, the at least some of the particles having a first average pore size in the interior region and a second average pore size at the surface region, and the first average pore size being greater than the second average pore size; and
    a carrier fluid, the plurality of particles being in the carrier fluid.

17. The composition of claim 16, wherein the at least some of the particles have an average diameter of about 10 microns or more.

18. The composition of claim 16, wherein the at least some of the particles have an average diameter of about 100 microns or more.

19. The composition of claim 18, wherein the at least some of the particles have an average diameter of about 300 microns or less.

20. The composition of claim 16, wherein the at least some of the particles have an average a diameter of about 300 microns or more.

21. The composition of claim 16, wherein the at least some of the particles comprise about 2.5 weight percent or less of the polysaccharide.

22. The composition of claim 21, wherein the polysaccharide comprises alginate.

23. The composition of claim 16, wherein the at least some of the particles further comprise cross-linked polyvinyl alcohol.

* * * * *

UNITED STATES PATENT AND TRADEMARK OFFICE
CERTIFICATE OF CORRECTION

| | | |
|---|---|---|
| PATENT NO. | : 7,842,377 B2 | Page 1 of 1 |
| APPLICATION NO. | : 12/236051 | |
| DATED | : November 30, 2010 | |
| INVENTOR(S) | : Janel Lanphere et al. | |

It is certified that error appears in the above-identified patent and that said Letters Patent is hereby corrected as shown below:

1.) Cover Page, (75) Inventors: after "Janel Lanphere", Delete "Newton, MA" and Insert --Flagstaff, AZ--.

2.) Column 20, Line 23, Claim 20: after "average", Delete "a".

Signed and Sealed this
Fifteenth Day of March, 2011

David J. Kappos
*Director of the United States Patent and Trademark Office*